United States Patent
Gazit et al.

(10) Patent No.: US 12,042,791 B2
(45) Date of Patent: Jul. 23, 2024

(54) METHOD OF OSTEOGENIC DIFFERENTIATION IN MICROFLUIDIC TISSUE CULTURE SYSTEMS

(71) Applicant: Cedars-Sinai Medical Center, Los Angeles, CA (US)

(72) Inventors: Dan Gazit, Los Angeles, CA (US);
Gadi Pelled, Los Angeles, CA (US);
Zulma Gazit, Los Angeles, CA (US);
Dmitriy Sheyn, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 360 days.

(21) Appl. No.: 15/958,976

(22) Filed: Apr. 20, 2018

(65) Prior Publication Data

US 2018/0237741 A1    Aug. 23, 2018

Related U.S. Application Data

(63) Continuation-in-part of application No. PCT/US2017/013250, filed on Jan. 12, 2017.

(60) Provisional application No. 62/277,857, filed on Jan. 12, 2016.

(51) Int. Cl.
| | |
|---|---|
| *C12N 5/00* | (2006.01) |
| *A61K 49/00* | (2006.01) |
| *A61K 51/02* | (2006.01) |
| *A61L 27/38* | (2006.01) |
| *B01L 3/00* | (2006.01) |
| *C12N 5/071* | (2010.01) |
| *C12N 5/074* | (2010.01) |
| *C12N 5/077* | (2010.01) |
| *C12N 5/0775* | (2010.01) |
| *G01N 33/50* | (2006.01) |
| *G01T 1/164* | (2006.01) |
| *G01T 1/29* | (2006.01) |
| *C07K 14/78* | (2006.01) |
| *C12M 1/34* | (2006.01) |

(52) U.S. Cl.
CPC ........ *B01L 3/5027* (2013.01); *A61K 49/0019* (2013.01); *A61K 49/005* (2013.01); *A61K 51/02* (2013.01); *A61L 27/3895* (2013.01); *B01L 3/5085* (2013.01); *C12N 5/0062* (2013.01); *C12N 5/0075* (2013.01); *C12N 5/0654* (2013.01); *C12N 5/0655* (2013.01); *C12N 5/0662* (2013.01); *C12N 5/0663* (2013.01); *C12N 5/0668* (2013.01); *C12N 5/0696* (2013.01); *C12N 5/0697* (2013.01); *G01N 33/5038* (2013.01); *G01T 1/1644* (2013.01); *G01T 1/2985* (2013.01); *A61M 2205/3334* (2013.01); *C07K 14/78* (2013.01); *C12M 41/40* (2013.01)

(58) Field of Classification Search
None
See application file for complete search history.

(56) References Cited

U.S. PATENT DOCUMENTS

| | | | |
|---|---|---|---|
| 6,300,080 B1 | 10/2001 | Brenner et al. | |
| 7,989,197 B2 | 8/2011 | Yoo et al. | |
| 8,647,861 B2 | 2/2014 | Ingber et al. | |
| 9,790,470 B2 | 10/2017 | Vallier et al. | |
| 10,174,289 B2 | 1/2019 | Wells et al. | |
| 11,326,149 B2 | 5/2022 | Kerns et al. | |
| 2004/0247571 A1 | 12/2004 | Meijer et al. | |
| 2007/0077649 A1 | 4/2007 | Sammak et al. | |
| 2007/0128722 A1 | 6/2007 | Lin | |
| 2007/0281353 A1 | 12/2007 | Vacanti et al. | |
| 2008/0044847 A1 | 2/2008 | Shusta et al. | |
| 2008/0132445 A1 | 6/2008 | Ormandy et al. | |
| 2008/0305086 A1 | 12/2008 | Poole | |
| 2009/0075374 A1 | 3/2009 | Palecek et al. | |
| 2009/0123383 A1 | 5/2009 | Frangioni | |
| 2009/0214649 A1* | 8/2009 | Gazit | A61L 27/3604 435/325 |
| 2009/0258337 A1 | 10/2009 | Yagi | |
| 2009/0317852 A1 | 12/2009 | Parker et al. | |
| 2009/0324559 A1 | 12/2009 | Sakurada et al. | |

(Continued)

FOREIGN PATENT DOCUMENTS

| | | |
|---|---|---|
| AU | 2015204375 A1 | 8/2015 |
| AU | 2016341880 A1 | 5/2018 |

(Continued)

OTHER PUBLICATIONS

Park et al. "Chip-based comparison of the osteogenesis of human bone marrow-and adipose tissue-derived mesenchymal stem cells under mechanical stimulation." PloS one 7.9 (2012): e46689. (Year: 2012).*

(Continued)

*Primary Examiner* — Emily A Cordas
(74) *Attorney, Agent, or Firm* — NIXON PEABODY LLP

(57) ABSTRACT

Microfluidic "organ-on-a-chip" devices have been developed with the aim to replicate human tissues in vitro. However, there is no option to quantitatively monitor biological processes that take place within the chip, over time. Destructive methods in order to analyze, tissue formation, gene expression, protein secretion etc. require the harvest of the "tissue" at a certain time point. Described herein are methods and compositions for non-destructive molecular imaging methods and systems in order to quantitatively monitor specific biological processes, over time, within the chip, without the need to harvest.

21 Claims, 10 Drawing Sheets

(56) References Cited

U.S. PATENT DOCUMENTS

| | | |
|---|---|---|
| 2010/0136690 A1 | 6/2010 | Sundstorm et al. |
| 2011/0064700 A1 | 3/2011 | Cardozo et al. |
| 2011/0097796 A1 | 4/2011 | Loa |
| 2011/0111499 A1* | 5/2011 | Torihashi ............... A61P 21/00 435/325 |
| 2011/0245307 A1 | 10/2011 | Alkon |
| 2011/0250585 A1 | 10/2011 | Ingber et al. |
| 2012/0094381 A1 | 4/2012 | Chambers et al. |
| 2012/0107934 A1 | 5/2012 | Poole |
| 2012/0128655 A1 | 5/2012 | Kim et al. |
| 2012/0171354 A1 | 7/2012 | O'Neill et al. |
| 2012/0211373 A1 | 8/2012 | El-Sayed et al. |
| 2013/0137130 A1 | 5/2013 | Wells et al. |
| 2013/0224857 A1 | 8/2013 | Blak et al. |
| 2013/0280802 A1 | 10/2013 | Schulz et al. |
| 2013/0288969 A1 | 10/2013 | Scadden |
| 2014/0038279 A1 | 2/2014 | Ingber et al. |
| 2014/0065660 A1 | 3/2014 | Hanseup et al. |
| 2014/0093905 A1 | 4/2014 | Ingber et al. |
| 2014/0134732 A1 | 5/2014 | Ashton |
| 2014/0142370 A1 | 5/2014 | Wong et al. |
| 2014/0171380 A1 | 6/2014 | Kim et al. |
| 2014/0199700 A1 | 7/2014 | Kume et al. |
| 2014/0248621 A1 | 9/2014 | Collins |
| 2014/0288093 A1 | 9/2014 | Krainc et al. |
| 2014/0315990 A1 | 10/2014 | Alkon et al. |
| 2014/0329321 A1 | 11/2014 | Rajesh et al. |
| 2014/0342445 A1 | 11/2014 | Ingber et al. |
| 2015/0017674 A1 | 1/2015 | Christensen et al. |
| 2015/0023928 A1 | 1/2015 | Hassiotou |
| 2015/0037320 A1 | 2/2015 | McGrath et al. |
| 2015/0151011 A1 | 6/2015 | Jang et al. |
| 2015/0218522 A1 | 8/2015 | Peterson et al. |
| 2015/0232810 A1 | 8/2015 | Luo et al. |
| 2015/0252328 A1 | 9/2015 | Woodruff et al. |
| 2015/0258124 A1 | 9/2015 | Katajisto et al. |
| 2015/0265652 A1 | 9/2015 | George et al. |
| 2015/0329828 A1 | 11/2015 | Rezania |
| 2016/0145642 A1 | 5/2016 | Cui et al. |
| 2016/0152950 A1 | 6/2016 | Zhang et al. |
| 2016/0175401 A1 | 6/2016 | Spiegelman et al. |
| 2017/0107498 A1 | 4/2017 | Sareen et al. |
| 2017/0226478 A1 | 8/2017 | Kerns et al. |
| 2017/0240866 A1 | 8/2017 | Wells et al. |
| 2017/0253856 A1 | 9/2017 | Douvaras et al. |
| 2017/0283772 A1 | 10/2017 | Qian et al. |
| 2017/0292116 A1 | 10/2017 | Erlls et al. |
| 2017/0313976 A1 | 11/2017 | Kuwahara et al. |
| 2018/0021383 A1 | 1/2018 | George et al. |
| 2018/0057788 A1 | 3/2018 | Kerns et al. |
| 2018/0237741 A1 | 8/2018 | Gazit et al. |
| 2018/0298331 A1 | 10/2018 | Kerns et al. |
| 2018/0298332 A1 | 10/2018 | Kerns et al. |
| 2018/0305651 A1 | 10/2018 | Kerns et al. |
| 2018/0305668 A1 | 10/2018 | Gazit et al. |
| 2019/0009270 A1 | 1/2019 | Gazit et al. |
| 2019/0018000 A1 | 1/2019 | Gazit et al. |
| 2019/0031992 A1 | 1/2019 | Kerns et al. |
| 2019/0153395 A1 | 5/2019 | Barrett et al. |
| 2019/0194606 A1 | 6/2019 | Vatine et al. |
| 2019/0359924 A1 | 11/2019 | Kerns et al. |
| 2020/0000267 A1 | 1/2020 | Zuidervaart et al. |
| 2020/0002671 A1 | 1/2020 | Qu et al. |
| 2020/0032215 A1 | 1/2020 | Svendsen et al. |
| 2020/0071673 A1 | 3/2020 | Sareen et al. |
| 2020/0157508 A1 | 5/2020 | Barrett et al. |
| 2021/0000880 A1 | 1/2021 | Svendsen et al. |
| 2021/0023039 A1 | 1/2021 | Laperle et al. |
| 2021/0024886 A1 | 1/2021 | Laperle et al. |
| 2021/0033628 A1 | 2/2021 | Laperle et al. |
| 2021/0130774 A1 | 5/2021 | Sances et al. |
| 2023/0159896 A1 | 5/2023 | Sharma et al. |
| 2024/0067933 A1 | 2/2024 | Laperle et al. |
| 2024/0076629 A1 | 3/2024 | Laperle et al. |

FOREIGN PATENT DOCUMENTS

| | | |
|---|---|---|
| AU | 2017213795 A1 | 8/2018 |
| AU | 2017214468 A1 | 9/2018 |
| AU | 2017319168 A1 | 3/2019 |
| AU | 2017321489 A1 | 3/2019 |
| AU | 2018235950 A1 | 10/2019 |
| AU | 2018236273 A1 | 10/2019 |
| AU | 2018270270 A1 | 12/2019 |
| AU | 2017319168 B2 | 4/2021 |
| AU | 2016341880 B2 | 5/2021 |
| CA | 3002399 A1 | 4/2017 |
| CA | 3013337 A1 | 8/2017 |
| CA | 3013357 A1 | 8/2017 |
| CA | 3034614 A1 | 3/2018 |
| CA | 3035058 A1 | 3/2018 |
| CA | 3055992 A1 | 9/2018 |
| CA | 3056089 A1 | 9/2018 |
| CA | 3064086 A1 | 11/2018 |
| EP | 3008168 A1 | 4/2016 |
| EP | 3031908 A1 | 6/2016 |
| EP | 3365424 | 8/2018 |
| EP | 3411470 A2 | 12/2018 |
| EP | 3411472 A1 | 12/2018 |
| EP | 3503901 A1 | 7/2019 |
| EP | 3504319 A1 | 7/2019 |
| EP | 3625331 A1 | 3/2020 |
| EP | 3768823 | 1/2021 |
| EP | 3775161 | 2/2021 |
| EP | 3787613 | 3/2021 |
| EP | 3787649 A1 | 3/2021 |
| EP | 4048282 | 8/2022 |
| GB | 2561312 A | 10/2018 |
| GB | 2562406 A | 11/2018 |
| GB | 2564582 A | 1/2019 |
| GB | 2568446 A | 5/2019 |
| GB | 2569058 A | 6/2019 |
| GB | 2574988 A | 12/2019 |
| GB | 2575574 A | 1/2020 |
| GB | 2561312 B | 3/2021 |
| GB | 2564582 B | 9/2021 |
| HK | 1260726 B | 7/2021 |
| HK | 1260726 B2 | 7/2021 |
| JP | 2003-511346 | 9/2000 |
| JP | 2014-171434 A | 9/2014 |
| JP | 2014171434 | 9/2014 |
| JP | 2015-504676 A | 2/2015 |
| JP | 2015504676 | 2/2015 |
| JP | 2018533940 A | 11/2018 |
| JP | 2019506861 A | 3/2019 |
| JP | 2021-520784 A1 | 8/2021 |
| JP | 2021-523700 A1 | 9/2021 |
| JP | 2021-523888 A1 | 9/2021 |
| KR | 20180069882 A | 6/2018 |
| KR | 10-2022-0084282 | 6/2022 |
| SG | 11201803143 Y | 5/2018 |
| SG | 11201901621V | 3/2019 |
| SG | 11201901628 | 3/2019 |
| SG | 11201908358 P | 10/2019 |
| SG | 11201908359 U | 10/2019 |
| WO | 2000053218 | 9/2000 |
| WO | 2005021720 A2 | 3/2005 |
| WO | WO 2005/021720 A2 | 3/2005 |
| WO | 2010009307 A2 | 1/2010 |
| WO | WO 2010/108005 A2 | 9/2010 |
| WO | 2011109440 A1 | 9/2011 |
| WO | 2012/100084 A1 | 7/2012 |
| WO | WO 2012/118799 A2 | 9/2012 |
| WO | 2013/056216 A1 | 4/2013 |
| WO | 2013/071282 A1 | 5/2013 |
| WO | WO 2013/065763 A1 | 5/2013 |
| WO | 2013/086486 A1 | 6/2013 |
| WO | 2013106677 A1 | 7/2013 |
| WO | 2013/184193 A1 | 12/2013 |
| WO | 2014159356 A1 | 10/2014 |
| WO | 2014172682 A1 | 10/2014 |
| WO | WO 2014/172682 A1 | 10/2014 |
| WO | WO 2014/176606 A1 | 10/2014 |
| WO | WO 2015/052143 A1 | 4/2015 |

(56) References Cited

FOREIGN PATENT DOCUMENTS

| | | |
|---|---|---|
| WO | WO 2015/057261 A1 | 4/2015 |
| WO | 2015126528 A1 | 8/2015 |
| WO | WO 2015/126528 A1 | 8/2015 |
| WO | 2015143342 A1 | 9/2015 |
| WO | WO 2015/138032 A2 | 9/2015 |
| WO | WO 2015/138034 A2 | 9/2015 |
| WO | 2015153451 A1 | 10/2015 |
| WO | WO 2015/163823 A1 | 10/2015 |
| WO | WO 2015/181253 A1 | 12/2015 |
| WO | WO 2015/183920 A2 | 12/2015 |
| WO | WO 2015/188131 A1 | 12/2015 |
| WO | 016063985 A1 | 4/2016 |
| WO | 2016061464 A1 | 4/2016 |
| WO | WO 2016/086040 A1 | 6/2016 |
| WO | WO 2016/093222 A | 6/2016 |
| WO | 2016/141137 A1 | 9/2016 |
| WO | 2016162747 A2 | 10/2016 |
| WO | 2016183252 A1 | 11/2016 |
| WO | WO 2017/035119 A1 | 3/2017 |
| WO | WO 2017/070224 A1 | 4/2017 |
| WO | 2017075271 A1 | 5/2017 |
| WO | 2017078807 A1 | 5/2017 |
| WO | WO 2017/075271 A1 | 5/2017 |
| WO | 2017/112455 A1 | 6/2017 |
| WO | 2017123806 A1 | 7/2017 |
| WO | WO 2017/123806 A1 | 7/2017 |
| WO | WO 2017/136462 A2 | 8/2017 |
| WO | WO 2017/136479 A1 | 8/2017 |
| WO | WO 2017/143049 A1 | 8/2017 |
| WO | WO 2017/200486 A1 | 11/2017 |
| WO | 2017/219000 A1 | 12/2017 |
| WO | 2018/035214 A1 | 2/2018 |
| WO | WO 2018/044885 A1 | 3/2018 |
| WO | WO 2018/044934 A1 | 3/2018 |
| WO | 2018/140647 A2 | 8/2018 |
| WO | 2018/176001 A1 | 9/2018 |
| WO | WO 2018/170139 A1 | 9/2018 |
| WO | WO 2018/170180 A1 | 9/2018 |
| WO | WO 2018/213773 A1 | 11/2018 |
| WO | 2019/122291 A1 | 6/2019 |
| WO | 2019/178550 A1 | 9/2019 |
| WO | 2019169351 A1 | 9/2019 |
| WO | WO 2019/183597 A1 | 9/2019 |
| WO | 2019195798 A1 | 10/2019 |
| WO | 2019195800 A1 | 10/2019 |
| WO | WO 2019/195798 A1 | 10/2019 |
| WO | 2019212690 A1 | 11/2019 |
| WO | 2019212691 A1 | 11/2019 |
| WO | 2021/081229 A1 | 4/2021 |
| WO | 2021/081237 A1 | 4/2021 |
| WO | 2021222724 A1 | 11/2021 |

OTHER PUBLICATIONS

Fridley et al. "Hydrodynamic modulation of pluripotent stem cells." Stem cell research & therapy 3.6 (2012): 45. (Year: 2012).*
Zhang et al. "Patient-specific 3D microfluidic tissue model for multiple myeloma." Tissue Engineering Part C: Methods 20.8 (2014): 663-670. (Year: 2014).*
Lee et al. "Microfluidic 3D bone tissue model for high-throughput evaluation of wound-healing and infection-preventing biomaterials." Biomaterials 33.4 (2012): 999-1006. (Year: 2012).*
Gao et al. "Regulation of cell migration and osteogenic differentiation in mesenchymal stem cells under extremely low fluidic shear stress." Biomicrofluidics 8.5 (2014): 052008. (Year: 2014).*
Halim et al. "Recent progress in engineering mesenchymal stem cell differentiation." Stem Cell Reviews and Reports 16.4 (2020): 661-674. (Year: 2020).*
Bai et al. "BMP-2, VEGF and bFGF synergistically promote the osteogenic differentiation of rat bone marrow-derived mesenchymal stem cells." Biotechnology Letters 35.3 (2013): 301-308. (Year: 2013).*
Sun et al. "Role of bone morphogenetic protein-2 in osteogenic differentiation of mesenchymal stem cells." Molecular medicine reports 12.3 (2015): 4230-4237. (Year: 2015).*
Hojo et al. "Development of high-throughput screening system for osteogenic drugs using a cell-based sensor." Biochemical and biophysical research communications 376.2 (2008): 375-379. (Year: 2008).*
International Search Report and Written Opinion of PCT Application No. PCT/US2017/013250, Dated Mar. 31, 2017, 12 Pages.
International Search Report and Written Opinion of PCT Application No. PCT/US2016/057724, Dated Jan. 9, 2017, 17 Pages.
International Search Report and Written Opinion of PCT/US2017/016098, Dated Jun. 22, 2017, 14 Pages.
International Search Report and Written Opinion of PCT/US2017/016079, Dated Jul. 25, 2017, 26 Pages.
International Search Report and Written Opinion of PCT/US2017/049193, Dated Nov. 6, 2017, 9 Pages.
International Search Report and Written Opinion of PCT/US2017/049115, Dated Nov. 28, 2017, 11 Pages.
International Search Report and Written Opinion of PCT/US2018/022511, Dated Jul. 26, 2018, 11 Pages.
International Search Report and Written Opinion of PCT/US2018/033498, Dated Aug. 9, 2018, 9 Pages.
International Search Report and Written Opinion for PCT/US2018/022455 dated Aug. 23, 2018, 13 pages.
International Preliminary Report on Patentability for PCT/US2016/057724 dated Apr. 24, 2018, 15 pages.
International Preliminary Report on Patentability for PCT/US2018/022455 dated Aug. 23, 2018, 9 pages.
International Search Report and Written Opinion of PCT/US2019/023749, Dated Jun. 25, 2019, 12 Pages.
AU 2016341880 Examination Report dated Jan. 15, 2020, 5 pages.
AU 2017214468 Examination Report dated Dec. 10, 2019, 5 pages.
CA 3034614 Examination Report dated Jul. 5, 2019, 5 pages.
EP 16858141.1 Extended Search Report dated Mar. 15, 2019, 10 pages.
EP 17748100.9 European Partial Supplementary Search Report dated Sep. 18, 2019, 15 pages.
EP 17748100.9 European Extended Search Report dated Dec. 20, 2019, 12 pages.
EP 17748084.5 European Extended Search Report dated Sep. 10, 2019.
EP 17847396.3 European Extended Search Report dated, Jan. 28, 2020, 11 pages.
EP17847365.8 European Extended Search Report dated Jan. 21, 2020, 11 pages.
GB1811716.8 Examination Report dated Feb. 12, 2020, 6 pages.
GB 1903007.1 Search Report dated Apr. 1, 2019, 8 pages.
SG 11201803143Y Search Report dated Jul. 15, 2019, 3 pages.
Action Potential, Wikipedia, pp. 1-29 Downloaded on Apr. 28, 2019, https://en.wikipedia.org/wiki/Action_potential.
Adriani et al,. Modeling the Blood-Brain Barrier in a 3D Triple Co-Culture Microfluidic System, 37th Annual International Conference of the IEEE Engineering in Medicine and Biology Society, IEEE, pp. 338-341.
Armstrong et al., Human Induced Pluripotent Stem Cell Lines Show Stress Defense Mechanisms and Mitochondrial Regulation Similar to Those of Human Embryonic Stem Cells, 2010, Stem Cells, vol. 28(4), pp. 661-673.
Barrett et al., Reliable Generation of Induced Pluripotent Stem Cells from Human Pymphoblastoid Cell Lines, 2014, Stem Cells Translational Medicine, vol. 3, pp. 1429-1434.
Ben-Zvi et al., Modeling Human Nutrition Using Human Embryonic Stem Cells, Cell, 2015, vol. 161(1), pp. 12-17.
Bhatia et al., Microfluidic Organs-on-Chips, Nature Biotechnology, 2014, vol. 32(8), pp. 760-772.
Booth, Ross Hunter, A Microfluidic in Vitro Model of the Blood-Brain Barrier, Dissertation, 2014, pp. 1-177.
Boyer et al., More than a Bystander: The Contributions of Intrinsic Skeletal Muscle Defects in Motor Neuron Diseases, 2013, Frontiers in Physiology, vol. 4, Article 356, pp. 1-12.

(56) References Cited

OTHER PUBLICATIONS

Brown et al., Recreating Blood-Brain Barrier Physiology and Structure on Chip: A Novel Neurovascular Microfluidic Bioreactor, 2015, Biomicrofluidics, vol. 9(5).
Cashman et al., Induced Pluripotent Stem Cells and Motor Neuron Disease: Toward an Era of Individualized Medicine, J. Neurosci, 2013, vol. 33, pp. 8587-8589.
Chal et al., Differentiation of Pluripotent Stem Cells to Muscle Fiber to Model Duchenne Muscular Dystrophy, 2015, Nature Biotechnology, vol. 33(9), pp. 962-969.
Chen et al., Surface Marker Epithelial Cell Adhesion Molecule and E-Cadherin Facilitate the Identification and Selection of Induced Pluripotent Stem Cells, 2011, Stem Cell Rev., vol. 7(3), pp. 722-735.
Date et al., Mini-Gut Organoids: Reconstruction of the Stem Cell Niche, Annu. Rev. Cell Dev. Biol., 2015, vol. 31, pp. 269-289.
Dhumpa et al., Temporal Gradients in Microfluidic Systems to Probe Cellular Dynamics: A Review, Anal. Chim. Acta, 2012, vol. 743, pp. 9-18.
Dimos et al., Induced Pluripotent Stem Cells Generated from Patients with ALS can be Differentiated into Motor Nuerons, Science, 2008, vol. 321, pp. 1218-1221.
Douville et al., Fabrication of Two-Layered Channel System with Embedded Electrodes to Measure Resistance Across Epithelial and Endothelial Barriers, 2010, Analytical Chemistry, vol. 82(6), pp. 2505-2511.
Ebert et al., EZ Spheres: A Stable and Expandable Culture System for the Generation of Pre-rosette Multipotent Stem Cells from Human ESCs and iPSCs., 2013, Stem Cell Research, vol. 10(3), pp. 417-427.
Esch et al., Organs-on-Chips at the Frontiers of Drig Discovery, Nature Reviews, 2015, vol. 14(4), pp. 248-269.
Evans et al., The Development of a Method for the Preparation of Rat Intestinal Epithelial Cell Primary Cultures, 1992, Journal of Cell Science, vol. 101, pp. 219-231.
Gao et al., Regulation of Cell Migration and Osteogenic Differentiation in Mesenchymal Stem Cells under Extremely Low Fluidic Shear Stress, Biomicrofluidics, 2014, vol. 8(5), Article No. 052008.
Gel, Wikipedia, pp. 1-29 Downloaded on Sep. 14, 2018, https://en.wikipedia.org/wiki/Gel.
Gracz et al., CD24 and CD44 Mark Human Intestinal Epithelial Cell Populations with Characteristics of Active and Facultative Stem Cells, 2013, Stem Cells, vol. 31(9), pp. 2024-2030.
Gross et al., Applications of Microfluidics for Neuronal Studies, 2007, Journal of the Neurological Sciences, vol. 252, pp. 135-143.
Hu et al. Neural differentiation of human induced pluripotent stem cells follows developmental principles but with variable potency, PNAS, 2010, vol. 107(9), pp. 4335-4340.
Hu et al., Derivation, Expansion and Motor Neuron Differentiation of Human-Induced Pluripotent Stem Cells with Non-Integrating Episomal Vectors and a Defined Xenogeneic-Free Culture System, Mol Neurobiol, 2016, vol. 53, pp. 1589-1600.
Hughes et al., Matrigel: A Complex Protein Mixture Required for Optimal Growth of Cell Culture, 2010, Proteomics, vol. 10, pp. 1886-1890.
Huh et al., From 3D Cell Culture to Organs-on-Chips, Trends in Cell Biology, 2011, vol. 21(2), pp. 745-754.
Huh et al., Microfabrication of Human Organs-on-Chips, Nature Protocols, 2013, vol. 8(11), pp. 2135-2157.
Hynds et al., Concise Review: The Relevance of Human Stem Cell-Derived Organoid Models for Epithelial Transitional Medicine, Stem Cells, 2013, vol. 1 31, pp. 417-422.
Jang et al., JAK-STAT Pathway and Myogenic Differentiation, JAKSTAT, 2013, vol. 2(2), pp. e23282-1 to e-23282-6.
Joo-Eun, L., Patient-Specific Induced Pluripotent Stem Cell Models of Variant Angina Derived from Peripheral Blood, The Department of Biomedical Sciences Seoul National University College of Medicine, Jul. 2017, pp. 1-75.
Kilic et al., Brain-on-a-Chip Model Enables Analysis of Human Neuronal Differentiation and Chemotaxis, 2016, Lab on a Chip, vol. 16(21), pp. 4152-4162.
Kim et al., Human Gut-on-a-Chip Inhabited by a Microbial Flora that Experiences Intestinal Peristalsis-Like Motions and Flow, Lab on a Chip, 2012, vol. 12(12). pp. 2165.
Kim et al., Gut-on-a-Chip Microenvironmental Induces Human Intestinal Cells to Undergo Villus Differentiation, Integrative Biology, 2013, vol. 5(9), p. 1130-1140.
Kim et al., Contributions of Microbiome and Mechanical Deformation to Intestinal Bacterial Overgrowth and Inflammation in a Human Gut-on-a-Chip, PNAS, 2015, vol. 113(1), pp. E7-E15.
Kirkby et al., A Role for Correlated Spontaneous Activity in the Assembly of Neural Circuits, 2013, Neuron, vol. 80(5), 27 Pages.
Lenner, J., Fat Cells More Easily Programmed into iPS Cells, 2009, pp. 1-2.
Lin et al., Neural Stem Cell Differentiation in a Cell-Collagen-Bioreactor Culture System, 2004, Developmental Brain Research, vol. 153, pp. 163-173.
Lippmann, et al., Human Blood-Brain Barrier Endothelial Cells Derived from Pluripotent Stem Cells, 2012, Nature Biotechnology, vol. 30(8), pp. 783-791.
Lippmann et al., A Retinoic Acid-Enhanced, Multicellular Human Blood-Brain Barrier Model Derived from Stem Cell Sources, Scientific Reports, vol. 4(1), 2014, pp. 1-10.
Lippmann et al., Chemically Defined Differentiation of Human Pluripotent Stem Cells to Hindbrain and Spinal Cord Neural Stem Cells with Defined Regional Identifies, 2015, Protocol Exchange.
Martin et al., Laparoscopic Colorectal Resection in the Obese Patient, 2011, Clinics in Colon and Rectal Surgery, vol. 24(4), pp. 263-273.
Massumi et al., Efficient Programming of Human Eye Conjunctiva-Derived Induced Pluripotent Stem (ECiPS) Cells into Definitive Endoderm-Like Cells, Experimental Cell Research, 2014, vol. 322, pp. 51-61.
Medical Dictionary—Myotube, Downloaded on Jul. 8, 2018, https://medical-dictionary.thefreedictionary.com/myotube, p. 1.
Murphy et al., Scaffolds for 3D in vitro Culture of Neural Lineage Cells, Acta Biomaterialia, 2017, vol. 54, pp. 1-20.
Nicoleau et al., Embryonic Stem Cells Neural Differentiation Qualifies the Role of Wnt/[beta]-Catenin Signals in Human Telecephalic Specification and Regionalization: Human ESC Telencephalic Differentiation, Stem Cells, 2013, vol. 31(9), pp. 1763-1774.
Niego et al., Improved Method for the Preparation of a Human Cell-based, Contact Model of the Blood-Brain Barrier, 2013, J. Vis. Exp., vol. 81(e50934), pp. 1-9.
Nostro et al., Efficient Generation of NKX6-1+ Pancreatic Progenitors from Multiple Human Pluripotent Stem Cell Lines, Stem Cell Reports, 2015 4(4), pp. 591-604.
Ochetta et al., High-Throughput Microfluidic Platform for 3D Cultures of Mesenchymal Stem Cells, Towards Engineering Developmental Processes, Scientific Reports, 2015, vol. 5, Article No. 10288, pp. 1-12.
Okita et al., A More Efficient Method to Generate Integration-Free Human iPS Cells, 2011, Nature Methods, vol. 8(5), pp. 409-412.
Ong et al., A Gel-Free 3D Microfluidic Cell Culture System, Biomaterials, 2008, vol. 29, pp. 3237-3244.
Park et al., Chip-Based Comparison of the Osteogenesis of Human Bone Marrow and Adipose Tissue-Derived Mesenchymal Stem Cells under Mechanical Stimulation, PLOS One, 2012, vol. 7(9), pp. 1-12.
Polini et al., Organs-on-a-Chip: A New Tool for Drug Discovery, Expert Opinion on Drug Discovery, 2014, vol. 9(4), pp. 335-352.
Prabhakarpandian et al., SyM-BBB: A Microfluidic Blood Brain Barrier Model, Lab on a Chip, 2013, vol. 13(6), p. 1093.
Qian et al., A Simple and Efficient System for Regulating Gene Expression in Human Pluripotent Stem Cells and Derivatives, Stem Cells, 2014, vol. 32(5), pp. 1230-1238.
Rajesh et al., Human Lymphoblastoid B-Cell Lines Reprogrammed to EBV-FREE Induced Pluripotent Stem Cells, 2011, Blood, vol. 118(7), pp. 1797-1800.
Rhee et al., Patterned Cell Culture Inside Microfluidic Devices, Lab Chip, 2005, vol. 5(1), pp. 102-107.

(56) References Cited

OTHER PUBLICATIONS

Roberts et al., Expression of the Thyroid Hormone Transports Monocarboxylate Transporter-8 (SLC16A2) and Organic Ion Transporter-14 (SLCO1C1) at the Blood-Brain Barrier, Endocrinol, 2008, vol. 149(12), pp. 6251-6261.
Rosenberg et al., Calcium Signaling in Neuronal Development, 2011, Cold Spring Harb Perspect Biol., vol. 3(a004259), 13 Pages.
Sareen et al., Human Neural Progenitor Cells Generated from Induced Pluripotent Stem Cells can Survive, Migrate, and Integrate in the Rodent Spinal Cord, Journal of Comparative Neurology, 2014, vol. 522(12), pp. 2707-2728.
Sareen et al., Targeting RNA foci in iPSC-Derived Motor Neurons from ALS Patients with C90RF72 Repeat Expansion, 2013, Science Translational Medicine, vol. 5(208), 208ra149, 26 Pages.
Shimojo et al., Rapid, Efficient and Simple Motor Neuron Differentiation from Human Pluripotent Stem Cells, Molecular Brain, 2015, vol. 8(1), pp. 1-15.
Shimuzu et al., Microfluidic Devices for Construction of Contractile Skeletal Muscle Microtissues, J. Biosci. Bioeng., 2015, vol. 119, pp. 212-216.
Soria-Valles et al., NF-kB Activation Impairs Somatic Cell Reprogramming in Ageing, 2015, Nat. Cell Biol., vol. 17(8), pp. 1004-1013.
Stepniewski et al., Induced Pluripotent Stem Cells as a Model for Diabetes Investigation, Scientific Reports, 2015, 5:8597, 14 pages.
Telias et al., Electrical Maturation of Neurons Derived from Human Embryonic Stem Cells, F1000 Research, 2014, vol. 3(196), p. 1-12.
Tenstad et al., Extensive Adipogenic and Osteogenic Differentiation of Patterned Human Mesenchymal Stem Cells in a Microfluidic Device, Lab on a Chip, 2010, vol. 10(11), pp. 1401-1409.
Uzel et al., New Microfluidic Chip Replicates Muscle-Nerve Connection, 2016, Science Daily, pp. 1-4.
Vatine et al., Human iPSC-Derived Blood-Brain Barrier Chips Enable Disease Modeling and Personalized Medicine Applications, Cell Stem Cell, 2019, vol. 24(6), pp. 995-1005.
Vatine et al., Human iPSC-Derived Blood-Brain Barrier Chips Enable Disease Modeling and Personalized Medicine Applications, Cell Stem Cell, 2019, vol. 24, Supplemental Figures, p. 1-10.
Wang et al., Androgen Receptor-Mediated Apoptosis in Bovine Testicular Induced Pluripotent Stem Cells in Response to Phthalate Esters, 2013, Cell Death Dis., vol. 4(e907), pp. 1-11.
Wang et al., Modeling the Mitochondrial Cardiomyopathy of Barth Syndrome with Induced Pluripotent Stem Cell and Heart-on-Chip Technologies, Nature Medicine, 2014, vol. 20(6), pp. 616-623.
Watson et al., Modelling the Endothelial Blood-CNS Barriers: A Method for the Production of Robust in Vitro Models of the Rat Blood-Brain Barrier and Blood-Spinal Cord Barrier, 2013, BMC Neuroscience, vol. 14(59), pp. 1-21.
Wehkamp et al., Reduced Paneth Cell [alpha]-Defensins in Ileal Crohn's Disease, PNAS, 2005, vol. 102, pp. 18129-18134.
Workman et al., Enhanced Utilization of Induced Pluripotent Stem Cell-Derived Human Intestinal Organoids Using Microengineered Chips, CMGH Cellular and Molecular Gastroenterology and Hepatology, 2018, vol. 5(4), pp. 669-677.
Yamamoto et al., Fluid Shear Stress Induces Differentiation of Flk-1-positive Embryonic Stem Cells into Vascular Endothelial Cells in vitro., 2004, Am. J. Physiol. Heart Circ. Physiol., vol. 288, pp. 1915-1924.
Zilio et al., Universal Hydrophilic Coating of Thermoplastic Polymers Currently Used in Microfluidics, 2014, Biomed. Microdevices, vol. 16(1), pp. 107-114.
EP 19771249.0 Partial Supplemental European Search Report dated Nov. 8, 2021, 15 pages.
EP 18802136.4 Examination Report dated Oct. 14, 2021, 8 pages.
Demers et al., Development-on-Chip: in vitro Neutral Tube Patterning with a Microfluidic Device, Development, 2016, vol. 143(11), pp. 1884-1892.
Loo et al., An Arduous Journey from Human Pluripotent Stem Cells to Functional Pancreatic Beta Cells, Diabetes Obes Metab., 2018, vol. 20(3), pp. 3-13.

McGaugh et al., Efficient Differentiation of Pluripotent Stem Cells to NKX6-1 + Pancreating Progenitors, Journal of Visualized Experiments, 2017, vol. 121, pp. 1-5.
Ryan et al., Progranulin is expressed within motor neurons and promotes neuronal cell survival, BMC Neuroscience, 2009, 10:130, pp. 1-22.
Sances et al., Modeling ALS with Motor Neurons Derived from Human Induced Pluripotent Stem Cells, Nature Neuroscience, 2016, vol. 19, pp. 542-553.
Santaguida et al., Side by Side Comparison Between Dynamic Versus Static Models of Blood-Brain-Barrier in vitro: A Permeability Study, Brain Research, 2006, vol. 1109(1), pp. 1-13.
Schiesser et al., Derivation of Insulin-Producing Beta-Cells from Human Pluripotent Stem Cells, The Review of Diabetic Studies, 2014, vol. 11(1), pp. 6-18.
Schwartz et al., Allan-Herndon-Dudley Syndrome and the Monocarboxylate Transporter 8 (MCT8) Gene, 2005, AJHG, vol. 77(1), pp. 41-53.
Southam et al., A Novel in vitro Primary Culture Model of the Lower Motor Neuron -Nueromuscular Junction Circuit, Microfludic and Compartmentalized Platforms for Neurobiological Research, Humana Press, 2015, pp. 181-193, abstract only.
Uzei et al., Microfluidic Device for the Formation of Optically Excitable, Three-Dimensional, Compartmentalized Motor Units, Science Advances, 2016, pp. e1501429.
Wang et al., Generation of an Induced Pluripotent Stem Cell Line (SHCDNi003-A) from a One-Year Old Chinese Han Infant with Allan-Herndon-Dudley Syndrome, Stem Cell Research, 2020, vol. 46, 4 pages.
Jenke et al., DNA Methylation Analysis in the Intestinal Epithelium—Effect of Cell Separation on Gene Expression an Methylation Profile, PLOS One, 2013, vol. 8(2), pp. 1-8.
Brittan et al., The gastrointestial stem cell, Cell Prolif., 2004, vol. 37, pp. 35-53.
GB 1903007.1 Search Report dated Jun. 24, 2020, 8 pages.
Yamamoto et al., The Stabilization Effect of Mesenchymal Stem Cells on the Formation of Microvascular Networks in a Microfluidic Device, Journal of Biomechanical Science and Engineering, 2013, vol. 8(2).
Danmark et al., Development of a novel microfluidic device for long-term in situ monitoring of live cells in 3-dimensional matrices, Biomed Microdevices, 2012, pp. 885-893.
Yu et al., A Microfluidic-Based Multi-Shear Device for Investigating the Effects of Low Fluid-Induced Stresses on Osteoblasts, PLOS One, 2014, vol. 9(2), pp. 1-7.
ISR-WO—for PCT/US2019/026193 Jul. 1, 2019, 8 pages.
JP Notice of Reasons for Rejection dated Mar. 1, 2021.
Extended European Search Report for EP 18802136.4 dated Jan. 22, 2021, 12 pages.
Kuratnik et al., Intestinal organoids at tissue surrogates for toxicological and pharmacological studies, biochemical Pharmacology, Apr. 25, 2013, vol. 85:12, pp. 1721-1726.
Workman et al., Intestine-Chip: A new model to understand the role of the Intestinal Epithelium in IBD by combining Microengineering Technology and IPSC-Derived human intestinal organoids, Gastroenterology, Apr. 1, 2017, vol. 152:5, Abstract only.
Written Opinion 11201901628X Mar. 10, 2021, 9 pages.
Amoroso M. W. et al., Accelerated High-Yield Generation of Limb-Innervating Motor Neurons from Human Stem Cells. J Neurosci, Jan. 9, 2013, vol. 33, No. 2, pp. 574-586 pp. 575 and 578, Fig. 1 and 2.
Faravelli I. et al., Motor neuron derivation from human embryonic and induced pluripotent stem cells: Experimental approaches and clinical perspectives. Stem Cell Res Ther, Jul. 14, 2014, vol. 5, No. 4, pp. 87.
Jha et al., Motor Neuron differentiation from Pluripotent Stem Cells and Other Intermediate Proliferative Precursors that can be Discriminated by Lineage Specific Reports, Stem Cell Rev Rep, Aug. 2014, 11:194-204.
International Search Report and Written Opinion of PCT/US2019/26178, Dated Jun. 11, 2019, 14 Pages.
ISR-WO—for PCT/US2019/026195 Jun. 12, 2019, 10 pages.

(56) References Cited

OTHER PUBLICATIONS

Kondo, T. et al., Ipsc-based Coound screening and in vitro trials identify a synergistic anti-amyloid b combination for Alzheimer's Disease, Cell Reports, 2017, vol. 21, pp. 2304-2312.
McKinney, C.E. et al., Using induced pluripotent stem cells derived neurons to model brain diseases, Neural Regeneration Research, 2017, 12:7 pp. 1-11.
Li, Y. et al., Protein kinase C controls lysosome biogenesis independently of mTORC1, Nature Cell Biology, 2016, 10:10, pp. 1-26.
Kilpatrick, K. et al., Genetic and chemical activation of TFEB mediates clearance of aggregated a-synuclein, PLoS One, 2015, 10:3, pp. 1-21.
Chou, B.K. et al., Efficient human iPS cell derivation by a non-integrating plasmid from blood cells with unique epigenetic and gene eIDS filed Oct. 3, 2020pression signatures, Cell Research, 2011, 21:3, pp. 518-529.
Sundberg, m. et al., Improved cell therapy protocol for Parkinson's Disease based on differentiation efficiency and safety of Hesc-, Hipsc and non-human primate Ipsc-derived DA neurons, Stem Cells, 2013, 31:8, pp. 1-25.
International Search Report and Written Opinion of PCT/US2019/26183, Dated Jun. 12, 2019, 10 Pages.
Kauffman et al., Alternative functional in vitro models of human intestinal epithelia, frontiers in Pharmacology, Jul. 2013, vol. 4, Article 79, 18 pages.
Kelamangalath et al. k-Opioid receptor inhibition of calcium oscillations in spinal cord neurons,, Molecular Pharmacology, 2011, 79:1061-1071.
Kwasny et al., Static biofilm cultures of gram-positive pathogens grown in a microtiter format used for anti-biofilm drug discovery, Current Protocols in Pharmacology, 2010, 13A.8.1-13A.8.23.
Naik et al., In vitro blood-brain models: Current and perspective technologies, J. Phar Sci., 2012, 1014(4):1337-1354.
Wang et al., Microfluidics: A new cosset for neurobiology, Lab Chip, 2009, 9:644-652.
Abbott et al., Structure and function of the blood-brain barrier, Pharm Tox BBB: 1-3, Feb. 2010, Conf. Abstract.
Yang et al., From the vascular microenvironment to neurogenesis, Brain Res Bull. Jan. 15, 2011; 84(1):1-7.
Abbott et al., Structure and function of the blood-brain barrier, Neurobiology of Desease, 2010 27:13-25.
Perry et al., The Neuromuscular junction: Structure and function, downloaded from the internet (Neuromuscular junction: Parts, structure and steps/Kenhub>, pp. 1-6, downloaded Feb. 25, 2021.
Polydimethylsiloxane—Wikipedia, dowloaded on Feb. 24, 2021 <Silicon dioxide—Wikipedia>, pp. 1-11.
Silicon dioxide—Wikipedia, downloaded on Feb. 24, 2021 <silicon dioxide—Wikipedia> pp. 1-20.
Southam et al., Microfluidic primary culture model of the lower motor neuron-neuromuscular junction circuit, J Neurosc Meth 2013, 218:164-169.
DMEM F-12 Formulation, pp. 1-5, 2022.
Mehta et al., The actions of retinoids on cellular growth correlate with their actions on gap junctional communication, JCB 108, 1053-1065, 1989.
Essential 8 medium C037161 Essential8System Brochure (thermofisher. com), downloaded on Aug. 24, 2022, pp. 1-2.
ISR and WO for PCT/US2021/030128 mailed Aug. 25, 2021, 10 pages.
Ionescu et al., Compartmental microfluidic system for studying muscle-neuron communication and neuromuscular junction maintenance, 2016 European Journal of Cell Biology, 95:69-88.
International Search Report and Written Opinion for PCT/US2018/015318 May 2, 2018, 16 pages.
International Search Report and Written Opinion for PCT/US2018/024198 dated Aug. 13, 2018, 15 pages.
International Search Report and Written Opinion for PCT/US2020/056896 dated Oct. 22, 2020, 11 pages.
International Preliminary Report on Patentability for PCT/US2018/015318 dated Jul. 30, 2019, 12 pages.
International Preliminary Report on Patentability for PCT/US2018/024198 dated Feb. 25, 2020, 12 pages.
EP 19782199.4 Partial Supplementary Search Report dated Nov. 30, 2021, 15 pages.
EP 19796470.3 European Extended Search Report dated Dec. 10, 2021, 11 pages.
EP 19782199.4 Extended European Search Report dated Mar. 3, 2022, 12 pages.
EP 19796911.6 Extended Search Report dated Apr. 29, 2022, 15 pages.
Akhtar et al., Inducible Expression of GDNF in Transplanted iPSC-Derived Nueral Progenitor Cells, Stem Cell Reports, 2018, vol. 10, pp. 1696-1704.
Araoka, et al., Efficient and rapid induction of human iPSCs/ESCs into nephrogenic intermediate mesoderm using small molecule-based differentiation methods, PLoS One, 2014, 9(1), 14 pages.
Badger et al., Parkinson's disease in a dish Using stem cells as a molecular tool. Neuropharmacology, 2014, vol. 76, pp. 88-96.
Bai et al., BMP-2, VEGF and bFGF Synergistically Promote the Osteogenic Differentiation of Rat Bone Marrow-Derived Mesenchymal Stem Cells, Biotechnol Lett, 2013, vol. 35, pp. 301-308.
Bar-Am et al., Regulation of protein kinase C by the anti-Parkinson drug, MAO-B inhibitor, rasagiline and its derivatives, in vivo, Journal of Neurochemistry, 2004, vol. 89, No. 5, pp. 1119-1125.
Bohrnsen et al. Supportive angiogenic and osteogenic differentiation of mesenchymal stromal cells and endothelial cells in monolayer and co-cultures. International Journal of Oral Science (2016) 8, 223-230 (Year: 2016).
Burkhardt et al., A Cellular Model for Sporadic ALS using Patient-Derived Induced Pluripotent Stem Cells, Molecular and Cellular Neuroscience, 2013, vol. 56, pp. 355-364.
Chen, et al., Chemically defined conditions for human iPSC derivation and culture, 2011, Nat. Methods, 8(5), 8 pages.
Cooper et al., Differentiation of human ES and Parkinson's disease iPS cells into ventral midbrain dopaminergic neurons requires a high activity form of SHH, FGF8a and specific regionalization by retinoic acid, Molecular and Cellular Neurosciences, 2010, vol. 45, No. 3, pp. 258-266.
Farrelly et al., Extracellular matrix regulates apoptosis in mammary epithelium through a control on insulin signaling, The Journal of Cell Biology, 1999, 144(6):1337-1347.
Gurusamy et al., Hepatocyte Growth Factor-Like Protein is a Positive Regulator of Early Mammary Gland Ductal Morphogenesis, Mechanisms of Development, 2014, vol. 133, pp. 11-22.
Hens et al., BMP4 and PTHrP interact to stimulate ductal outgrowth during embryonic mammary development and to inhibit hair follicle induction, Development, 2017, 134:1221-1230.
Ichida et al., Probing disorders of the nervous system using reprogramming approaches, The EMBO Journal / European Molecular Biology Organization, 2015, vol. 34, No. 11, pp. 1456-1477.
Kessler et al., The Notch and Wnt pathways Regulate Stemness and Differentiation in Human Fallopian Tube Organoids, Nature Communications, 2015, vol. 6, p. 8989.
Kim et al. A practical guide to microfluidic perfusion culture of adherent mammalian cells. Lab Chip, 2007, 7, 681-694 (Year: 2007).
Kim et al. Shear Stress Induced by an Interstitial Level of Slow Flow Increases the Osteogenic Differentiation of Mesenchymal Stem Cells through TAZ Activation. PLoS ONE 9(3): e92427. p. 1-9 (Year: 2014).
Kitamura et al., Possible Involvement of Both Mitochondria and Endoplasmic Reticulum-Dependent Caspase Pathways in Retenone-Induced Apoptosis in Human Neuroblastoma SH-SY5Y Cells, Neuroscience Letters, 2002, vol. 2002, pp. 25-28.
Kreke et al. Effect of Intermittent Shear Stress on Mechanotransductive Signaling and Osteoblastic Differentiation of Bone Marrow Stromal Cells. Tissue Engineering: Part A vol. 14, No. 4, 2008. p. 529-537 (Year: 2008).
Lenzi et al., Differentiation of Control and ALS Mutant Human iPSCs into Functional Skeletal Muscle Cells, A Tool for the Study of Neuromuscolar Diseases, Stem Cell Research, 2016, vol. 17, pp. 140-147.

(56) References Cited

OTHER PUBLICATIONS

Levanon, et al., Primary ex vivo cultures of human fallopian tube epithelium as a model for serous ovarian carcinogenesis, Oncogene, 2010, 29(8):1103-1113.
Maegawa et al. Enhancement of osteoblastic differentiation of mesenchymal stromal cells cultured by selective combination of bone morphogenetic protein-2 (BMP-2) and fibroblast growth factor-2 (FGF-2). J Tissue Eng Regen Med 2007; 1: 306-313 (Year: 2007) Abstract Only.
Nishimura et al. Effect of osteogenic differentiation medium on proliferation and differentiation of human mesenchymal stem cells in threedimensional culture with radial flow bioreactor. Regenerative Therapy 2 (2015) 24-31 (Year: 2015).
O'Neill et al., Genetic disorders coupled to ROS deficiency, Redox Biology, 6: 135-156. (Year: 2015).
Qu et al., Differentiation of human induced pluripotent stem cells to mammary-like organoids, Stem Cell Reports, 2017, 8(2):205-215.
Rey, et al., Chapter 7, Sexual Differentiation, 2016 [online]. [Retrieved on Sep. 19, 2019]. Retrieved from the internet <URL:https://www.endotext.org/wp-content/uploads/pdfs/sexual-differentiation.pdf>, 89 pages.
Ryan et al., Isogenic Human iPSC Parkinson's Model Shows Nitrosative Stress-Induced Dysfunction in MEF2-PGCI [alpha] Trans, Cell, Elsevier, 2013, vol. 155, No. 6, pp. 1351-1364.
Sanchez-Danes et al., Disease-specific phenotypes in dopamine neurons from human iPS-based models of genetic and sporadic Parkinson's disease, EMBO Molecular Medicine, 2015, vol. 4, No. 5, pp. 380-395.
Simeone et al., The Otx Family, Pattern Formation and Development Mechanisms, 2002, vol. 12, pp. 409-415.
Sun et al., Role of Bone Morphogenetic Protein-2 in Osteogenic Differentiation of MesenChymal Stem Cells, Molecular Medicine Reports, 2015, vol. 12, pp. 4230-4237.
Tian et al., Salvianolic Acid B, An Antioxidant from Saliva Miltiorrhiza, prevents 6-hydroxydopamine Induced Apoptosis in SH-SY5Y Cells, The International Science Journal of Biochemistry & Cell Biology, 2008, vol. 40, pp. 409-422.
Vogel et al., Co-culture of human induced pluripotent stem cells 9iPSCs) with human fallopian tube epithelium (FTE) induces Pax8 and CK7 expression: Initial steps in modeling fallopian tube epithelium to study serous carcinogenesis; Gynecologic Oncology, 2015 137(1):206.
Wu et al., Nuclear Accumulation of Histone Deacetylase 4 (HDAC4) Exerts Neurotoxicity in Models of Parkinson's Disease, Moi Neurobiol, 2017, vol. 54, pp. 6970-6983.
Zhang et al., Regulation and Patterning of Cell Differentiation and Pluripotency, Thesis, Columbia University, pp. 1-177, 2011.
Zhang et al., FGF Ligands of the Postnatal Mammary Stroma Regulate Distinct Aspects of Epithelial Morphogenesis, Stem Cells and Regeneration, 2014, vol. 141, pp. 3352-3362.
Zhou et al., Rapid and efficient generation of transgene-free iPSC from a small vol. of cryopreserved blood, Stem Cell Reviews and Reports 11: 652-665. (Year: 2015).
PCT/US2020/056906 International Search Report and Written Opinion dated Mar. 16, 2021, 13 pages.
Arendt et al., Form and Function: how Estrogen and Progesterone Regulate the Mammary Epithelial Hierarchy, J. Mammary Gland Biol Neoplasia, 2015, 20:9-25.
Qiao et al, AP2y regulates neural and epiderman development downstream of the BMP pathway at early stages of ectodermal patterning, Cell Research, 2012, 22:1546-1561.
Lin et al., Embryoid body formation from human pluripotent stem cells in chemically defined E8 media, StemBook, ed, Jun. 1, 2014.
JP Reasons for Rejection—2020-560893 dated Feb. 6, 2023, 9 pages.
Matsumoto et al., Functional neurons generated from T Cell-derived induced pluripotent stem cells for neurological disease modeling, 2016, 6:422-435.
Moors et al., Therapeutic potential of autophagy-enhancing agents in Parkinson's disease, Molecular Neurodegeneration, 2017, 12:11, p. 1-18.
Okita et al., An efficient nonviral method to generate integration-free human-induced pluripotent stem cells from cord blood and peripheral blood cells, Stem Cells 2013, 31:458-466.
Kondo et al., iPSC-Based compound screening and in vitro trials identify a synergistic anti-amyloid B combination for Alzheimer's Disease, Cell Reports 2017, 21:2304-2312.
Kim, et al. [3-Cell regeneration through the transdifferentiation of pancreatic cells: Pancreatic progenitor cells in the pancreas, Journal of Diabetes Investigation 7(3): 286-296. doi: 10.1111/jdi .12475. (Year: 2016).
Clayton, et al., Generating induced pluripotent stem cell derived endothelial cells and induced endothelial cells for cardiovascular disease modelling and therapeutic angiogenesis, International Journal of Cardiology 197: 116-122. doi: 10.1016/ j.ijcard.2015.06.038.
Hayes et al., Strategies to generate induced pluripotentstem cells, Methods in Molecular Biology 1029: 77-92. doi: 10.1007/978-1-62703-478-4_6 (Year: 2013).
Shafa et al., Human-Induced Pluripotent Stem Cells Manufactured Using a Current Good Manufacturing Practice-Compliant Process Differentiate Into Clinically Relevant Cells From Three Germ Layers, Frontiers in Medicine 5: 69. doi: 10.3389/fmed.
Munera et al., Differentiation of Human Pluripotent Stem Cells into Colonic Organoids via Transient Activation of BMP Signaling, Cell Stem Cell, 21, 51-64, 2017.

\* cited by examiner

Figure 2
Fig. 2A
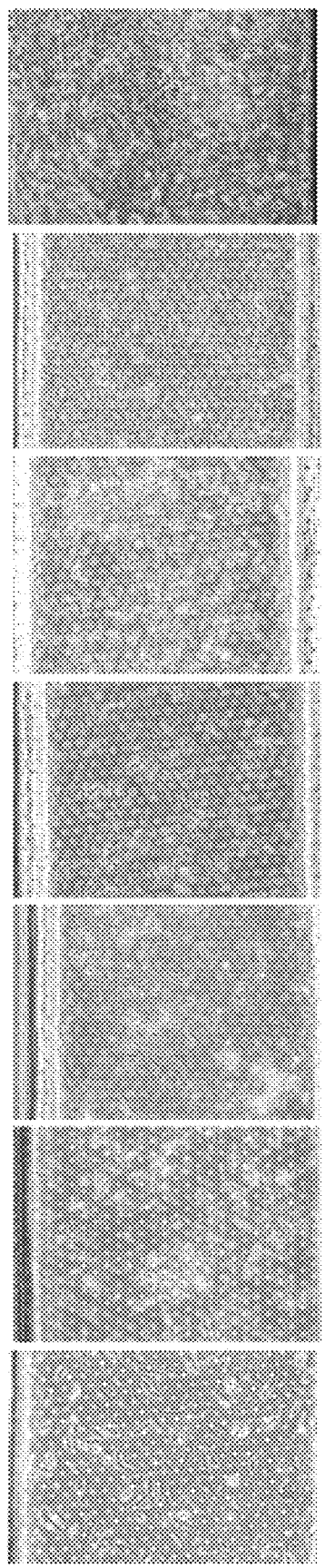
Fig. 2C
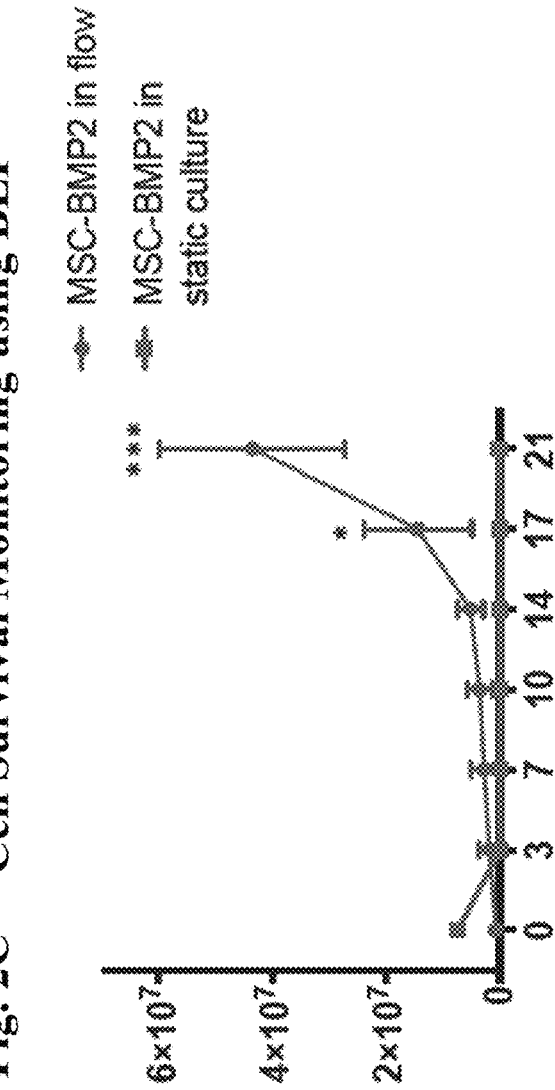
Fig. 2B
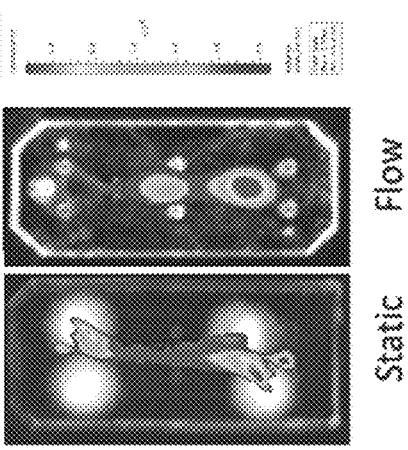

Figure 3
Fig. 3D
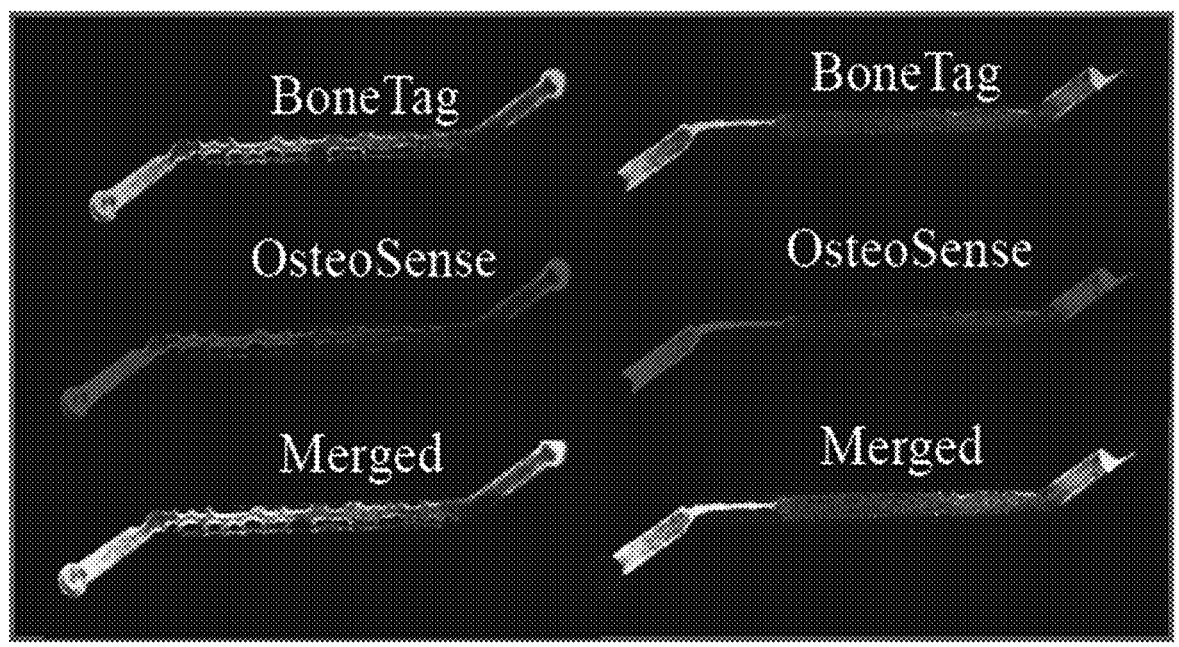
Osteogenesis quantified using NIR imaging
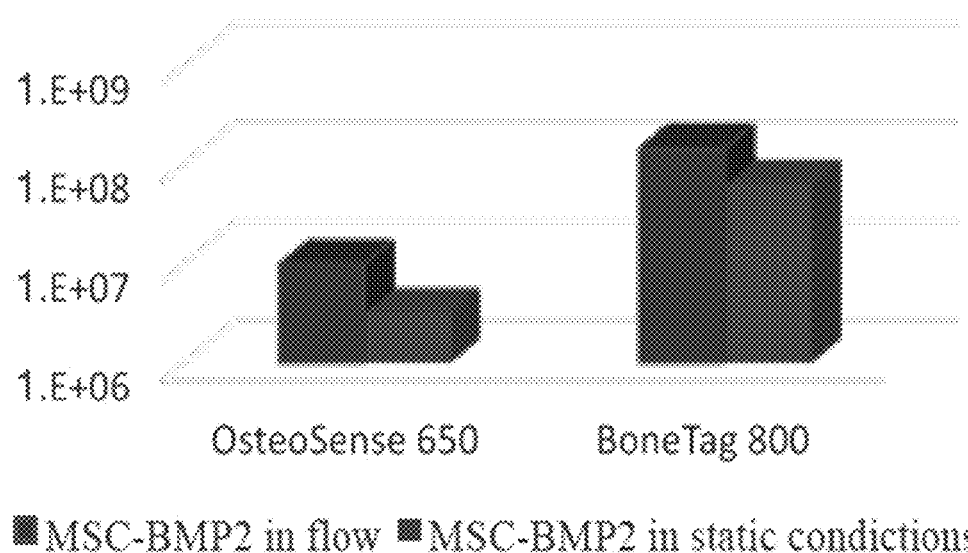
■ MSC-BMP2 in flow ■ MSC-BMP2 in static condictions

METHOD OF OSTEOGENIC DIFFERENTIATION IN MICROFLUIDIC TISSUE CULTURE SYSTEMS

CROSS REFERENCE TO RELATED APPLICATIONS

This application is a continuation-in-part of, and claims priority under 35 USC 111(a) to, co-pending International Patent Application No. PCT/US2017/013250, filed on Jan. 12, 2017, which claims priority to U.S. Provisional Application Ser. No. 62/277,857, filed on Jan. 12, 2016.

FIELD OF THE INVENTION

Described herein are methods and compositions related to imaging of stem cells and cells undergoing differentiation without sample manipulation.

BACKGROUND

Bones consisting of mineralized bone tissue also consists of bone marrow, nerves and blood vessels. Development and homeostasis of bone relies heavily on communication between cells in the tissues as regulated by the bone environment. Bone is an active tissue maintained by bone cells such as osteoblasts that form bone and osteoclasts that resorb bone, and it is now understood that mesenchymal stem cells (MSCs) can differentiate to various skeletal cells including osteoblasts, chondrocytes, fibroblasts, adipocytes, tenocytes, nucleus pulposus cells and more. Additionally, within the collagen and mineral matrix osteocytes are also embedded and respond to the bone environment. The balance between these cells is necessary to maintain bone function. Studying bone is a challenging field due to microarchitecture defining the bone environment, which involve the intricately dense structural composition of the bone morphology. Unlike other tissues that can be processed and prepared for experiments, including cultured cell lines, working with bone is difficult. Studying intracellular dynamics of the bone cells embedded within the mineralized tissue has proven to be a challenging task.

Compounding these challenges related to underlying properties of the cellular material, imaging cells at subcellular level within the bone environment is very difficult. Paraffin tissue slices are a long standing conventional approach to evaluate microarchitecture and bone morphology. However, sample manipulation leads to changes in biochemical properties of antigenicity and mineral structure. Newer strategies to image cells within the bone such as MPJ, Micro-CT or Ultrasound can image bone structure and recently cells, however these techniques are limited by their low resolution at the cellular level given the surrounding physiological environment.

Recent "organ-on-a-chip" technologies represent new and exciting opportunities for bone research. These devices include a microfluidic cell culture apparatus that is a more physiologically relevant in vitro model than cells cultured in dishes. Importantly, providing for continuously perfused chambers inhabited by living cells arranged to simulate tissue- and organ-level physiology allow for the culturing of bone cells in a format mirroring their physiological environment. By studying bone cell function and response in this manner, a 3D environment can reveal completely different cellular dynamics compared to 2D cultures. The availability of cellular tissue material in this format further provides new avenues for apply imaging approaches of bone microarchitecture to identify features previously unavailable in tissue cultures or at insufficient resolution in vivo. Real time imaging of the bone marrow niche within bone and fluorescent imaging of cells within the bone marrow niche has reportedly been achieved. Recent advancements in imaging techniques allows for the identification of osteocytes embedded in the bone matrix. However, determining the localization of cell types and protein expression dynamics of single cells within the bone is still very difficult. And more research is needed to identify intracellular protein activities of the cell bodies embedded within mineralized matrix.

Described herein is the use of non-destructive molecular imaging methods and systems in order to quantitatively monitor specific biological processes, over time, within the chip, without the need to harvest the tissue. Such methods can provide valuable data on developing tissues and their response to pharmaceutical, chemical and environmental agents.

SUMMARY OF THE INVENTION

Described herein is a method, including providing a microfluidic device including mesenchymal stem cells (MSCs), osteoblasts and/or osteocytes, adding one or more labeling agents to the microfluidic device, and detecting the labeling agent. In other embodiments, the microfluidic device further includes one or more channels for loading of a control sample. In other embodiments, the one or more labeling agents comprise bisphosphonate imaging agents. In other embodiments, the bisphosphonate imaging agent includes a pamidronate backbone with a fluorescent label. In other embodiments, the one or more labeling agents comprise a NHS ester. In other embodiments, the one or more labeling agents comprise a iminodiacetic acid group. In other embodiments, detecting the labeling agent includes fluorescent imaging. In other embodiments, detecting the labeling agent includes near infrared imaging. In other embodiments, detecting the labeling agent further includes comparison of the quantity of detected labeling agent with one or more control samples. In other embodiments, detecting the labeling agent measures cellular mineralization. In other embodiments, detecting the labeling agent measures cellular differentiation. In other embodiments, detecting the labeling agent measures metabolic function. In other embodiments, detecting the labeling agent measures inflammation. In other embodiments, the method includes addition of an exogenous factor. In other embodiments, the method includes further culturing of mesenchymal stem cells (MSCs), osteoblasts, osteocytes, chondrocytes, tenocytes, fibroblasts, notochordal cells, and/or nucleus pulposus cells in the microfluidic device. In other embodiments, the method includes further detection of the labeling agent. In other embodiments, the MSCs, osteoblasts and/or osteocytes are derived from induced pluripotent stem cells (iPSCs). In other embodiments, the iPSCs are derived from a subject afflicted with a disease or condition. In other embodiments, the disease is a skeletal disease or condition.

Also described herein is method of measuring cellular differentiation, including providing a microfluidic device including stem cells, progenitors or precursors, differentiating the stem cells, progenitor or precursors, adding one or more labeling agents to the microfluidic device, and detecting the labeling agent, wherein the labeling agent is capable of binding to a marker of cellular differentiation.

BRIEF DESCRIPTION OF FIGURES

FIG. 2. Cell survival and proliferation on the organ-on-chip. FIG. 2A. Micrographs of the cells on the chip grown for 3 weeks in osteogenic conditions. FIG. 2B. bioluminescent imaging (BLI) images taken on Day 0. FIG. 2C. Quantitative analysis BLI that was done twice a week for 3 weeks. Bars indicate standard deviation, n=5, *p<0.05; ***P<0.001.

FIG. 3A. FLI images of chips incubated with BONETAG™ (fluorescent imaging agent) and in FIG. 3B the labeling was quantified FIG. 3C. using fluorescent imaging IVIS® (in vivo imaging fluorescence and bioluminescence imaging) Live staining where live cells are stained with FITC (green) dye and OSTEOSENSE™ (fluorescent imaging agent) is depicted in red and imaged using confocal microscopy, 10× magnification. In FIG. 3D, labeling was quantified, bars indicate standard deviation, n=5, *p<0.05; ***P<0.001.

DEFINITIONS

Figure 1:
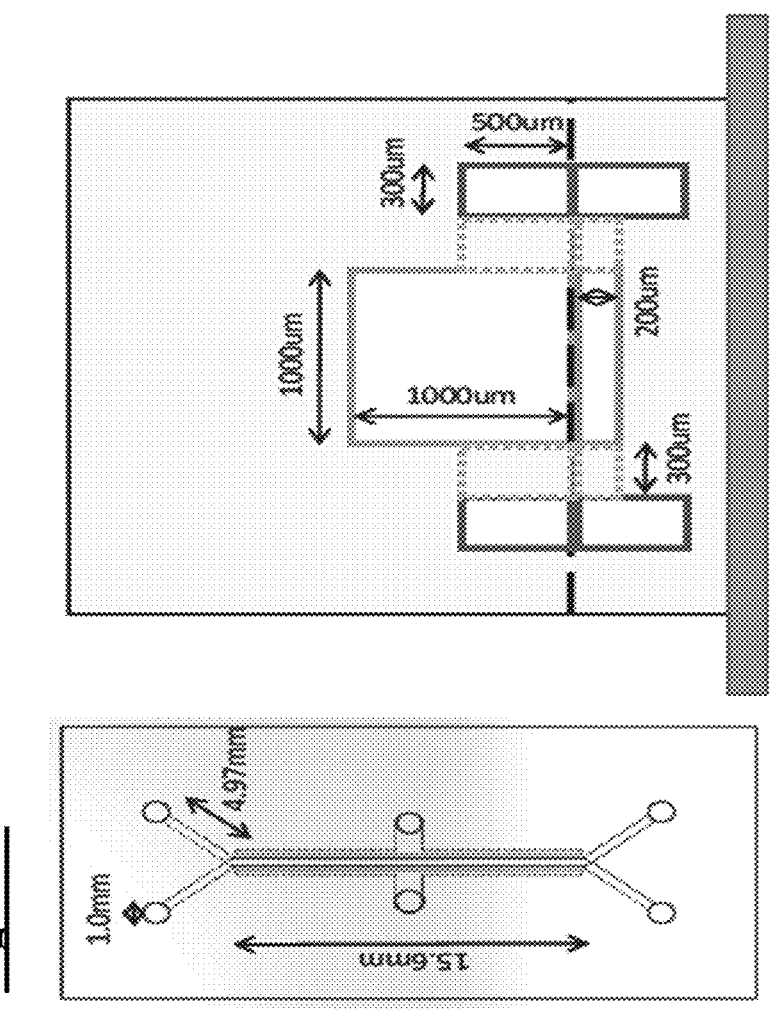
FIG. 1. Organ-on-chip dimensions and setting of the flow system. The flow was set to 30 µl/h and the media in the reservoirs was replaced or refilled twice a week.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

"Mesenchymal stem cells" ("MSCs") are an example of tissue or adult stem cells. They are "multipotent," meaning they can produce more than one type of specialized cell of the body, but not all types. MSCs make the different specialized cells found in the skeletal tissues.

The term "proliferation" refers to an increase in cell number.

The term "differentiation" refers to the maturation process cells undergo whereby they become specialized to develop distinctive characteristics and/or perform specific functions. In some embodiment, differentiated cells are less likely to divide than undifferentiated cells. Differentiation involves the production of cell-specific and/or tissue-specific proteins.

"Microfluidic" device refers to a device for manipulating fluids having a volume in the range of microliters ($10^{-6}$) to picoliters ($10^{12}$), and that contains at least one channel having at least one dimension of 10 μm or more.

"Confluence" and "confluent" as used herein in reference to adherent cells refers to a condition wherein cells throughout a culture are substantially in contact with each other creating what appears to be a continuous sheet, such as a "monolayer" of cells.

"Expression" refers to the process by which DNA is made into a functional gene product, such as protein or RNA. Expression may be detected by detecting the level of the transcribed RNA and/or the level of the translated protein.

"Laminin" refers to high-molecular weight (~400 to ~900 kDa) proteins of the extracellular matrix (ECM). Laminin is a major component of the basal lamina (one of the layers of the basement membrane), and is a protein network foundation for most cells and organs.

"Non-invasive" determination of the status of cells refers to the process of determining the condition (e.g., viability, protein expression, morphology, etc.) of the cells without harvesting the cells and/or without reducing cell viability and/or without structural and/or functional damage to the system in which the cells are contained.

The term "control" in reference to a sample (e.g., mixture of components, cell, etc.) refers to any type of sample that one of ordinary skill in the art may use for comparing to a test sample (e.g., cell, tissue, animal, virus, etc.) by maintaining the same conditions in the control and test samples, except in one or more particular variable factor or component. In one embodiment, the comparison of the control and test samples is used to infer a causal significance of this variable.

Figure 9:
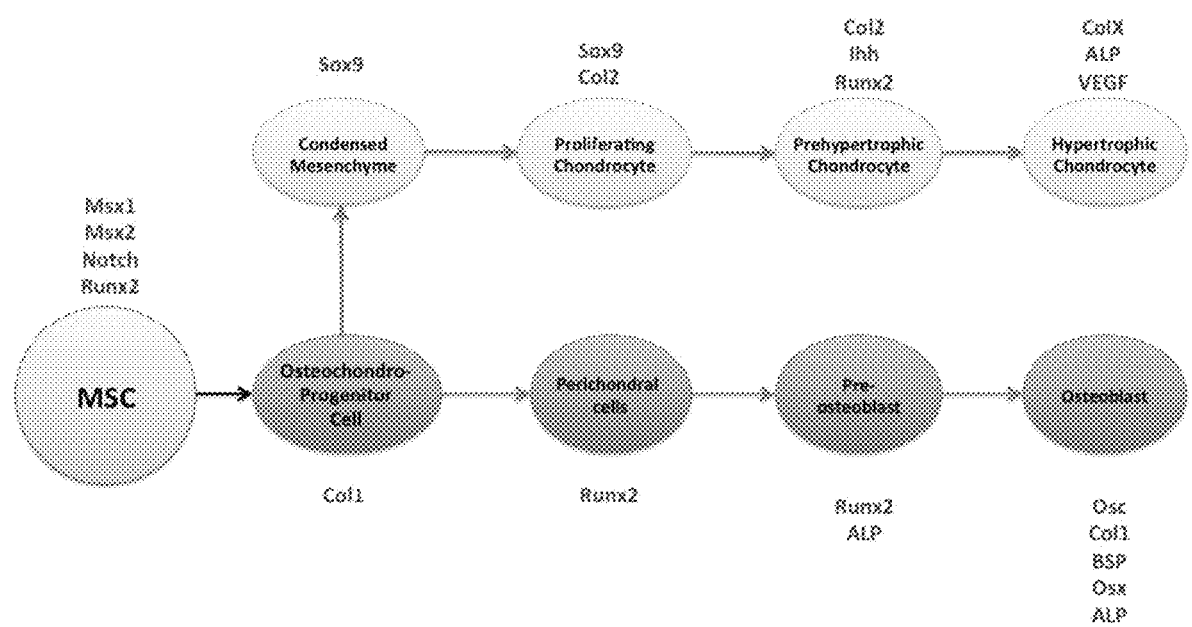
FIG. 9. Differentiation of MSCs into cells of the osteoblast lineage and chondrocyte lineage, including exemplary factors whose expression is elevated relative to one or more of the preceding cell types in the differentiation lineage.

"Osteoblast lineage" cell type refers to a cell that is produced during differentiation of mesenchymal stem cells (MSCs) into osteoblasts, and is exemplified by an osteochondro-progenitor cell expressing an increased level of Col1 compared to MSCs, perichondral cell expressing an increased level of Runx2 compared to an osteochondro-progenitor cell and/or MSC, pre-osteoblast expressing an increased level of Runx2 and/or ALP compared to perichondral cell and/or osteochondro-progenitor cell and/or MSC, and osteoblast expressing an increased level of Osc and/or Col1 and/or BSP and/or Osx and/or ALP compared to a pre-osteoblast and/or perichondral cell and/or osteochondro-progenitor cell and/or MSC (Exemplified in FIG. 9).

"Bone morphogenetic protein" and "BMP" refer to a BMP polypeptide or a fragment thereof that is similar or identical to the sequence of a wild-type BMP or fragment thereof. For example, a BMP polypeptide or fragment thereof has an amino acid sequence that is at least 70% or more (including at least 75%, at least 80%, at least 85%, at least 90%, at least 95%, at least 97%, at least 99%, or 100%) identical to that of a wild-type BMP, and is capable of having the normal functioning of BMP. The BMP used in the methods of various aspects described herein can be naturally occurring or recombinant protein or peptide.

"Matrix" refers to a collection of molecules (including polymers) that provide structural and/or biochemical support to the surrounding cells.

"Extracellular matrix" and "ECM" interchangeably refer to a matrix secreted by cells. In some embodiments, the ECM functions in enhancing cell adhesion and/or cell-to-cell communication and/or cell differentiation. ECM can be applied in two-dimensional (2D) cell culture to cover cell culture surfaces (e.g., membranes, solid supports, etc.) and/or in three-dimensional (3D) cell culture to encapsulate cells and/or tissue and/or organoids. ECM includes "natural ECM" and "synthetic ECM." "Natural ECM" and "native ECM" interchangeably refer to ECM in which the molecular components are derived from natural sources, and is exemplified by laminin, collagen, fibronectin, fibrin, vitronectin, hyaluronic acid, peptides, gelatin, and Matrigel®, decellularized matrix (e.g., decellularized bone marrow), and demineralized bone powder. Natural ECM is commercially available (East River Biosciences, MA, USA). "Synthetic ECM" refers to ECM containing man-made polymers, such as poly(ethylene glycol) (PEG), poly(vinyl alcohol), and poly(2-hydroxy ethyl methacrylate).

"Decellularized matrix" refers to a composition containing a molecules (including polymers) that are derived from or generated by removing the cellular components of an isolated population of cells and/or organs and/or tissues (e.g., bone marrow tissue) without significant damage to the extracellular matrix that is produced by the cells and/or organs and/or tissues. By way of non-limiting example, bone marrow cells can be removed from bone marrow tissue by chemical and/or physical means using methods known in the art for partially or completely decellularizing a tissue such as those described in Ingber et al. U.S. Pat. Appl. No. 20140186414, published Jul. 3, 2014, incorporated by reference. Briefly, cells can be removed and/or made nonviable by, for example, 1) washing the tissue with detergents or 2) washing the tissue with a buffer, then fixing the tissue with paraformaldehyde. In some embodiments, the tissue can be decellularized by fixing with 4% paraformaldehyde (PFA) for 48 hours at 4° C. and then immersing the microfluidic device and/or tissue in 70% ethanol for 24 hours at 4° C. and three times in PBS at 4° C. for 2 hours each time to wash out the PFA. The remaining decellularized bone marrow scaffold can be used ex vivo and/or in vitro and be repopulated by cells (such as bone marrow cells and/or blood cells) provided from another source.

"Demineralized bone powder," "demineralized bone matrix powder" and "DMB powder" can be obtained commercially (RTI Surgical). DMB powder can also be prepared using methods known in the art by excising, fragmenting, and sieving mammalian femurs (e.g., from mouse) to obtain particles less than 250 µm in diameter. The powder can then be demineralized using 0.5 N HCl (Eagle et al. "Production of an osteoinductive demineralised bone matrix powder without the use of organic solvents," Cell Tissue Bank. 2015 September; 16(3):433-41).

"Gel" refers to a coherent mass containing a liquid in which particles too small to be seen in an ordinary optical microscope are dispersed and/or arranged in a fine network throughout the mass. A gel may be notably elastic and jellylike (as gelatin or fruit jelly), or quite solid and rigid (as silica gel, a material that looks like coarse white sand). In one embodiment, gels are colloids (aggregates of fine particles, as described above, dispersed in a continuous medium) in which the liquid medium has become viscous enough to behave substantially as a solid.

"Mechanical stimulation" refers to one or more of compression, tension, shear, and hydrostatic loading that may be applied in constant and/or changing rates and/or magnitudes and/or amplitudes, and/or frequency, and/or loading duration and/or total duration to cells in a device, to alter cell proliferation, differentiation, gene expression, biochemistry, and/or biomechanics as shown in FIGS. 13-18, and previously described (Anderson & Johnstone, Bioeng. Biotechnol., 11 Dec. 2017, "Dynamic Mechanical Compression of Chondrocytes for Tissue Engineering: A Critical Review;" Tuan et al. U.S. Pat. Application No. 20160201037, incorporated by reference).

The terms "higher," "greater," "increase," "elevate," "raise," and grammatical equivalents when in reference to the level of any molecule (e.g., amino acid sequence such as osteocalcin, bone sialoprotein (bsp), osteopontin (opn), collagen type 1, runt-related transcription factor 2 (Runx2), alkaline phosphatase (ALP), Osc, and osterix (Osx), nucleic acid sequence such as a that encoding such as osteocalcin, bone sialoprotein (bsp), osteopontin (opn), collagen type 1, runt-related transcription factor 2 (Runx2), alkaline phosphatase (ALP), Osc, and osterix (Osx), etc.), cell, and/or phenomenon (e.g., level of gene transcription, level of RNA translation, level of protein expression, etc.), in a first sample relative to a second sample, mean that the quantity of the molecule, cell and/or phenomenon in the first sample is higher than in the second sample by any amount that is statistically significant using any art-accepted statistical method of analysis. In one embodiment, the first sample is exemplified by, but not limited to, a sample that has been manipulated using the invention's systems and/or compositions and/or methods. In a further embodiment, the second sample is exemplified by, but not limited to, a sample that has not been manipulated using the invention's compositions and/or methods, such as a control sample. In one embodiment, the quantity of the molecule, cell and/or phenomenon in the first sample is at least 10% greater than in the second sample, including from at least 10% greater to 1,000-fold greater than in the second sample. In one embodiment, the quantity of the molecule, cell and/or phenomenon in the first sample is at least 10% greater, at least 20% greater, at least 30% greater, at least 40% greater, at least 50% greater, at least 60% greater, at least 70% greater, at least 80% greater, at least 90% greater, at least 1-fold greater, at least 2-fold greater, at least 3-fold greater, at least 4-fold greater, at least 5-fold greater, at least 6-fold greater, at least 6-fold greater, at least 8-fold greater, at least 9-fold greater, at least 10-fold greater, at least 11-fold greater, at least 12-fold greater, at least 13-fold greater, at least 14-fold greater, at least 15-fold greater, at least 16-fold greater, at least 17-fold greater, at least 18-fold greater, at least 19-fold greater, and at least 20-fold greater than in the second sample.

DETAILED DESCRIPTION

All references cited herein are incorporated by reference in their entirety as though fully set forth. Unless defined otherwise, technical and scientific terms used herein have the same meaning as commonly understood by one of ordinary skill in the art to which this invention belongs. Allen et al, Remington: The Science and Practice of Pharmacy 22n d ed., Pharmaceutical Press (Sep. 15, 2012); Hornyak et al, Introduction to Nanoscience and Nanotechnology, CRC Press (2008); Singleton and Sainsbury, Dictionary of Microbiology and Molecular Biology $3^{rd}$ ed., revised ed., J. Wiley & Sons (New York, NY 2006); Smith, March's Advanced Organic Chemistry Reactions, Mechanisms and Structure $7^{th}$ ed., J. Wiley & Sons (New York, NY 2013); Singleton, Dictionary of DNA and Genome Technology $3^{rd}$ ed., Wiley-Blackwell (Nov. 28, 2012); and Green and Sambrook, Molecular Cloning: A Laboratory Manual 4th ed., Cold Spring Harbor Laboratory Press (Cold Spring Harbor, NY 2012), provide one skilled in the art with a general guide to many of the terms used in the present application. For references on how to prepare antibodies, see Greenfield, Antibodies A Laboratory Manual $2^{nd}$ ed., Cold Spring Harbor Press (Cold Spring Harbor NY, 2013); Kohler and Milstein, Derivation of specific antibody-producing tissue culture and tumor lines by cell fusion, Eur. J. Immunol. 1976 July, 6(7):511-9; Queen and Selick, Humanized immunoglobulins, U.S. Pat. No. 5,585,089 (1996 December); and Riechmann et al, Reshaping human antibodies for therapy, Nature 1988 Mar. 24, 332(6162):323-7.

One skilled in the art will recognize many methods and materials similar or equivalent to those described herein, which could be used in the practice of the present invention. Indeed, the present invention is in no way limited to the methods and materials described.

In recent years, microfluidic devices have been developed with the aim to replicate human tissues in vitro. These systems, also called microfluidic chips or "organ-on-a-chip", have the potential to serve as an alternative for animal models that are used to test pharmaceutical, chemical and environmental agents. The microfluidic chips are attractive for biomedical research and drug discovery due to low cost and ethical considerations compared to animal models. A variety of examples are described in Bhatia and Ingber, "Microfluidic organs-on-chips." Nat Biotechnol. 2014 August; 32(8):760-72, which is fully incorporated by reference herein.

An important caveat of the "chips" is that currently there is no option to quantitatively monitor biological processes that take place within the chip, over time. To date, researchers are using destructive methods in order to analyze tissue formation, gene expression, protein secretion etc. These methods include histology, immunofluorescence or PCR and require the harvest of the "tissue" at a certain time point. The use of non-destructive molecular imaging methods and systems in order to quantitatively monitor specific biological processes, over time, within the chip, without the need to harvest the tissue would be a significant improvement in the field. Such methods can provide valuable data on developing tissues and their response to pharmaceutical, chemical and environmental agents.

Mesenchymal stem cells (MSCs) can differentiate to various skeletal cells including osteoblasts, chondrocytes, fibroblasts, adipocytes, tenocytes, nucleus pulposus cells and more. In situ imaging, both in non-living and living specimens, have provided new insights, but for the above described reasons, quantitative experimental data requires destructive processing that may introduce bias, and lack temporal and spatial resolution. In this regard, microfluidic organ-on-a-chip coupled with non-destructive labeling and imaging techniques may allow precise capture of MSC, osteoblast and osteocyte cell populations in micro and ultrastructure in 2D and 3D. Live cell imaging techniques which are able to track structural morphology and cellular differentiation in both space and time combined with the latest biochemical assays and microfluidic imaging techniques can provide further insight on the biological function of MSC, MSCs, osteoblasts, osteocytes, chondrocytes, tenocytes, fibroblasts, notochordal cells, and/or nucleus pulposus cells.

Existing techniques for imaging of cells in skeletal and other tissues has proved challenging due to the need to develop methodologies for sectioning specimens, labeling or imaging of specimens or to develop protocols for decalcifying specimens to enable conventional sectioning and imaging techniques to be used. Current imaging approaches rely mainly on histological stains combined with conventional light microscopy. Confocal imaging approaches allows for three-dimensional (3D) imaging in situ within the bone environment. In contrast to inherently two-dimensional (2D) imaging techniques such as light microscopy, confocal microscopy stacks optical sections at different focal planes to generate a three-dimensional (3D) representation of the sample. Endogenous (auto)fluorescence of the bone tissue can be used to provide contrast for confocal microscopy measurements. More often, various fluorescent staining agents are used in conjunction with modern confocal laser scanning microscopy (CLSM), such as rhodamine and fluorescein, which can be incubated with undecalcified bone sections. More specific staining agents, such as fluorescein isothiocyanate (FITC)-conjugated phalloidin and DAPI, label the actin skeleton and/or DNA of cell nuclei in such a way that the components cells can be directly imaged and separately displayed in 3D However, a major drawback with CLSM is the limited maximum focal plane depth of around 100-150 μm. Additionally, CLSM is tainted with image artifacts, such as signal attenuation with increasing focal plane depth or aberrations due to refractive index mismatch. Such artifacts are absent in (conventional) X-ray absorption-based computed tomography (CT). Micro-computed CT (μCT) and 3D morphometric measures to quantify trabecular microarchitecture have laid the foundations for μCT to become a standard for bone morphometry. In bone research, the standard application of desktop μCT systems with typical voxel sizes in the order of 5-100 μπι is a core approach for quantitative characterization of whole bone geometry. Synchrotron radiation-based CT allows for imaging of bone microstructure, canal networks, as well as study of populations such as osteocytes within bone. Most recently, optimized imaging protocol for SR CT provides spatial resolution closer to the diffraction limit of visible light at a few hundred nanometers. The recent availability of desktop μCT scanners with voxel sizes below 1 μπι allow for new opportunities for imaging.

Over the past two decades or so, technologies for imaging of living cells using light and confocal microscopy have advanced at a rapid rate. Coupled with enhanced green fluorescent proteins (GFPs) and a seemingly limitless array of fluorescent imaging probes has made it possible to image almost any intracellular or extracellular structure or protein in living cells and tissues. A large selection of fluorescent probes and reagents are commercially available to the researcher for investigating biological events in living cells, including fluorescent antibodies, kits for fluorescently labeling proteins of interest, dyes for cell and nuclear tracking, probes for labeling of membranes and organelles, fluorescence reagents for determining cell viability, probes for assessing pH and ion flux and probes for monitoring enzyme activity, etc. In addition, a variety of GFP-derived fluorescent protein vectors are available that can either be used as reporter constructs or to generate fusion constructs with a protein of interest. These enable the live monitoring of gene expression and protein localization in vivo, and in real time.

The traditional approach of collecting "static" images of fixed or post mortem cells and tissues provides a snapshot view of events at a single fixed point in time. However, this inherently overlooks the dynamic aspects of the biology being examined. In contrast, live cell imaging enables the visualization of temporal changes in living specimens and can reveal novel aspects of the biology that may not otherwise have been appreciated. Additionally, the datasets generated from time-lapse imaging are information rich and can be interrogated quantitatively to enable measurement of cellular, subcellular and tissue dynamic events as a function of time Although these approaches are leading to exciting discoveries that are advancing our understanding of biological systems, there are several limitations that need to be acknowledged. Firstly, fluorescent probes may perturb or alter the biology being examined. Validation studies are needed to make sure that the fusion protein still functions similarly to the wild type form. It is also advantageous to confirm findings with more than one type of imaging probe if possible. For example, a GFP fusion protein can be used for in vivo localization of a specific protein and key data can be confirmed using a fluorescence-conjugated antibody against the same protein. When developing live cell imaging protocols, there is always a compromise between obtaining a high enough signal-to-noise ratio to enable quantitative measurements and to obtain sufficient image resolution, while at the same time avoiding phototoxic effects to the cells. Therefore, to ensure cell viability, the researcher may have to accept a lower image quality and resolution than would be acceptable for equivalent images of fixed specimens. Nevertheless, technologies such as multiphoton fluorescence microscopy can increase the depth of tissue penetration for live cell imaging applications and reduce phototoxicity by using a longer wavelength light to excite fluorophores. These instruments are becoming more widely used for live imaging applications due to their advantages over conventional widefield and confocal microscopy systems.

Recently, live cell imaging approaches have been applied to the study of MSCs, osteoblasts and osteocytes. Organ cultures of neonatal calvaria from mice have provided a useful model for imaging the dynamic properties of osteocytes. Another way in which this model can be used for imaging osteocyte dynamics is by using long term cultures of MSCs and osteoblasts. These cells differentiate when cultured under mineralizing conditions to form mineralized nodules in which the transition to the osteocyte-like phenotype can be monitored by fluorescent labeling or radiolabeling. To gain maximum information, imaging of these can be combined with other fluorescent probes, such as alizarin red to monitor mineral deposition. Live cell imaging studies as applied to investigating osteocyte biology are still in their infancy. In addition to revealing the dynamic properties of MSCs, osteoblasts and osteocytes, identifying the underlying intracellular signaling pathways, such as calcium oscillations, monitoring the temporal integration of osteocyte differentiation and mineralization, live imaging studies have considerable potential to address many as yet unresolved questions in osteocyte biology.

Most importantly, biochemical data characterizing the precise role of MSCs, osteoblasts and osteocytes in bone remodeling remains severely limited. A number of in vivo models have been developed to study their function. Existing technologies typically harvest large osteocyte populations and employ technologies which provide a comprehensive assessment of a large number of genes which are both up-regulated and down-regulated in response mechanical stimulation. For example, to comprehensively assess osteocyte gene expression in a mouse model for load induced bone adaptation, current state-of-the-art approaches extract large populations of osteocytes from loaded bone and perform micro-array-analysis to quantify the expression levels of tens of thousands of different genes. Global gene expression assays derived from in vivo models for bone adaptation have identified a number of candidate genes and revealed potential load regulated pathways. Nevertheless, there are significant limitations when interpreting these data. The harvesting and analysis of large populations of osteocytes reports gene expression averaged over tens of thousands of cells, each of which reside in different micro-environments characterized by different levels of mechanical strain and local osteoblastic/osteoclastic activity. It is therefore possible that key genes and networks are being concealed. Emerging studies investigate local regulation of gene expression in osteocytes by comparing 2D histology sections from loaded bone stained for specific molecular targets (sclerostin) with micro finite element (μFE) models. Whilst informative, these approaches are still very much qualitative and only permit the analysis of one specific molecular target at a time.

Addressing these limitations are microfluidic imaging approaches which allow for spatial and temporal mapping in three dimensions and quantitative measurement of gene expression cells in an organized "organ-on-a-chip" niche. Examples of a "microfluidic imaging" approach can be briefly described by the following workflow: bone formation and/or resorption are spatially mapped and quantified in technologies such as in vivo μCT and 3D image registration techniques; labeling (e.g., fluorescence, radio labeling) or other techniques, (e.g., chemical exchange saturation transfer (CEST), pH measurement T1rho, magnetization transfer contrast, magnetization exchange or other technologies. The vast amount of data generated using these approaches can be used to build, feed and validate computational models of various skeletal and other tissues, which incorporate all of the different length scales, from the organ-level to the cellular-level. Further examples include those described in Trussel et al., "Toward mechanical systems biology in bone." Ann Biomed Eng. 2012 November; 40(11):2475-87.

Described herein is a method, including providing a microfluidic device including mesenchymal stem cells (MSCs), osteoblasts and/or osteocytes, adding one or more labeling agents to the microfluidic device, and detecting the labeling agent. In other embodiments, the microfluidic device further includes one or more channels for loading of a control sample. In other embodiments, the MSCs, osteoblasts and/or osteocytes express a fluorescent reporter, such as luciferase. In other embodiments, the reporter is inducibly expressed. In other embodiments, the one or more labeling agents comprise bisphosphonate imaging agents. In other embodiments, the bisphosphonate imaging agent includes a pamidronate backbone with a fluorescent label. In other embodiments, the one or more labeling agents comprise a NHS ester. In other embodiments, the one or more labeling agents comprise a iminodiacetic acid group. In other embodiments, detecting the labeling agent or reporter includes fluorescent imaging. In other embodiments, detecting the labeling agent or reporter includes near infrared imaging. In other embodiments, detecting the labeling agent further includes comparison of the quantity of detected labeling agent with one or more control samples. In other embodiments, detecting the labeling agent measures cellular mineralization. In other embodiments, detecting the labeling agent measures cellular differentiation. In other embodiments, detecting the labeling agent measures metabolic function. In other embodiments, detecting the labeling agent measures inflammation. In other embodiments, the method includes addition of an exogenous factor. In other embodiments, the exogenous factor includes cytokines such as TNF-alpha and IL-17. In other embodiments, the exogenous factors include a therapeutic agent, such as parathyroid hormone. In other embodiments the method includes addition or alteration of liquid flow in the microfluidic device. In other embodiments, the method includes further culturing of mesenchymal stem cells (MSCs), osteoblasts, osteocytes, chondrocytes, tenocytes, fibroblasts, notochordal cells, and/or nucleus pulposus cells in the microfluidic device. In other embodiments, the method includes further detection of the labeling agent. In other embodiments, the MSCs, osteoblasts and/or osteocytes are derived from induced pluripotent stem cells (iPSCs). In other embodiments, the iPSCs are derived from a subject afflicted with a disease or condition. In other embodiments, the disease is a skeletal disease or condition. In other embodiments, the method includes collection of secretome from the microfluidic device. In other embodiments, the method includes analysis of the secretome.

Also described herein is method of measuring cellular differentiation, including providing a microfluidic device including stem cells, progenitors or precursors, differentiating the stem cells, progenitor or precursors, adding one or more labeling agents to the microfluidic device, and detecting the labeling agent, wherein the labeling agent is capable of binding to a marker of cellular differentiation. In other embodiments, the stem cells, progenitors or precursors include MSCs, osteoblasts and/or osteocytes. In other embodiments, the stem cells, progenitors or precursors express a fluorescent reporter, such as luciferase. In other embodiments, the reporter is inducibly expressed. In other embodiments, the one or more labeling agents comprise bisphosphonate imaging agents. In other embodiments, the bisphosphonate imaging agent includes a pamidronate backbone with a fluorescent label. In other embodiments, the one or more labeling agents comprise a NHS ester. In other embodiments, the one or more labeling agents comprise a iminodiacetic acid group. In other embodiments, detecting the labeling agent or reporter includes fluorescent imaging. In other embodiments, detecting the labeling agent or reporter includes near infrared imaging. In other embodiments, detecting the labeling agent further includes comparison of the quantity of detected labeling agent with one or more control samples. In other embodiments, cellular differentiation includes cellular mineralization. In other embodiments, cellular differentiation includes alterations in metabolic function, including for example production or lack of production of metabolites. In other embodiments, detecting the labeling agent measures inflammation. In other embodiments, the method includes addition of an exogenous factor. In other embodiments, the exogenous factor includes cytokines such as TNF-alpha and IL-17. In other embodiments, the exogenous factors include a therapeutic agent, such as parathyroid hormone. In other embodiments the method includes addition or alteration of liquid flow in the microfluidic device. In other embodiments, the method includes further culturing of mesenchymal stem cells (MSCs), osteoblasts, osteocytes, chondrocytes, tenocytes, fibroblasts, notochordal cells, and/or nucleus pulposus cells in the microfluidic device. In other embodiments, the method includes further detection of the labeling agent. In other embodiments, the MSCs, osteoblasts and/or osteocytes are derived from induced pluripotent stem cells (iPSCs). In other embodiments, the iPSCs are derived from a subject afflicted with a disease or condition. In other embodiments, the disease is a skeletal disease or condition. In other embodiments, the method includes collection of secretome from the microfluidic device. In other embodiments, the method includes analysis of the secretome.

Described herein is a method of detecting properties of one of more cells in a microfluidic device. In other embodiments, the microfluidic device includes mesenchymal stem cells (MSCs), osteoblasts and/or osteocytes. In other embodiments, the microfluidic device includes cartilage, tendon/ligament, nucleus pulposus, annulus fibrosus, chondrocytes, tenocytes, fibroblasts, and/or notochordal cells among others. It is emphasized that the described methods and techniques find wide applicability to biological tissues. In other embodiments, the microfluidic device includes stem cells. In other embodiments, the stem cells are mesenchymal stem cells (MSCs). In other embodiments, the stem cells are induced pluripotent stem cells (iPSCs). In other embodiments, the microfluidic device further includes one or more channels for loading of a control sample. In various embodiments, the properties are biochemical properties of the one or more cells in a microfluidic device.

In various embodiments, the method includes providing a microfluidic device, adding one or more labeling agents to the microfluidic device, and detecting the labeling agent, wherein the labeling agent is capable of binding to one or more biochemical properties of one or more cells in the microfluidic device. In other embodiments, one or more labeling agents comprise bisphosphonate imaging agents. In other embodiments, the bisphosphonate imaging agent includes a pamidronate backbone with a fluorescent label. In other embodiments, the one or more labeling agents comprise a radiolabel. In other embodiments, the radiolabel includes technetium-99m ([99mTc]-BPs), [18F]-Fluoride, 99mTc-Methyl diphosphonate (Tc-MDP), and/or 68Ga-Labeled (4-{[(bis(phosphonomethyl))carbamoyl]methyl}-7,1 O-bis(carboxymethyl)-I,4, 7, I 0-tetraazacyclododec-1-yl) acetic acid (BP AMD) ([68Ga]BPAMD). In other embodiments, detecting the labeling agent includes Micro CT, Micro SPECT, and/or PET imaging. In other embodiments, detecting the labeling agent further includes comparison of the quantity of detected labeling agent with one or more control samples. In other embodiments, the method includes further culturing of MSCs, osteoblasts and/or osteocytes in the microfluidic device. In other embodiments, the method includes further detection of the labeling agent.

In various embodiments, the method includes applying one or more pulse sequences to the microfluidic device, and detecting the pulse sequence signal intensity, wherein the pulse sequence signal intensity is capable of measuring one or more biochemical properties. In other embodiments, detecting the pulse sequence signal intensity includes chemical exchange saturation transfer (CEST), pH measurement of T1 rho, magnetization transfer contrast (MTC), and/or magnetization exchange (MEX). In other embodiments, CEST detects a quantity of glycosaminoglycans (GAGs). In other embodiments, pH measurement of T1 rho detects a quantity of GAGs. In other embodiments, MTC detects a quantity of collagen. In other embodiments, MEX detects a quantity of collagen and/or osteoid. In other embodiments, the microfluidic device further includes one or more channels for loading of a control sample. In other embodiments, detecting the pulse sequence signal intensity further includes comparison of the quantity of detected labeling agent with one or more control samples. In other embodiments, the method includes further culturing of stem cells in the microfluidic device. In other embodiments, the method includes further culturing of cartilage, tendon/ligament, nucleus pulposus, annulus fibrosus, chondrocytes, tenocytes, fibroblasts, and/or notochordal cells among others. In other embodiments, the method includes further detection of pulse sequence signal intensity. In various embodiments, the method includes detecting cellular mineralization. In other embodiments, the method includes detecting secreted extracellular macromolecules. In various embodiments, the method includes detecting cellular survival, differentiation and/or proliferation.

Described herein is a method of detecting cellular mineralization in a microfluidic device including providing a microfluidic device including mesenchymal stem cells (MSCs), osteoblasts and/or osteocytes, adding one or more labeling agents to the microfluidic device, and detecting the labeling agent, wherein the labeling agent is capable of binding to cellular mineralization. In other embodiments, the microfluidic device further includes one or more channels for loading of a control sample. In other embodiments, the one or more labeling agents comprise bisphosphonate imaging agents. In other embodiments, the bisphosphonate imaging agent includes a pamidronate backbone with a fluorescent label. In other embodiments, the one or more labeling agents comprise a radiolabel. In other embodiments, the radiolabel includes technetium-99m ([99mTc]-BPs), [18F]-Fluoride, 99mTc-Methyl diphosphonate (Tc-MDP), and/or 68Ga-Labeled (4-{[(bis(phosphonomethyl))carbamoyl] methyl}-7,1 O-bis(carboxymethyl)-I,4, 7, I 0-tetraazacyclododec-1-yl)acetic acid (BP AMD) ([68Ga]BPAMD). In other embodiments, detecting the labeling agent includes Micro CT, Micro SPECT, and/or PET imaging. In other embodiments, detecting the labeling agent further includes comparison of the quantity of detected labeling agent with one or more control samples. In other embodiments, the method includes further culturing of MSCs, osteoblasts and/or osteocytes in the microfluidic device. In other embodiments, the method includes further culturing cartilage, tendon/ligament, nucleus pulposus, annulus fibrosus, chondrocytes, tenocytes, fibroblasts, and/or notochordal cells in the microfluidic device. In other embodiments, the method includes further detection of the labeling agent.

Also described herein is method of detecting secreted extracellular macromolecules in a microfluidic device including providing a microfluidic device including stem cells, applying one or more pulse sequences to the microfluidic device, and detecting the pulse sequence signal intensity, wherein the pulse sequence signal intensity is capable of measuring one or more macromolecules secreted by the stem cells. In other embodiments, the stem cells are mesenchymal stem cells (MSCs). In other embodiments, the stem cells are induced pluripotent stem cells (iPSCs). In other embodiments, detecting the pulse sequence signal intensity includes chemical exchange saturation transfer (CEST), pH measurement of T1 rho, magnetization transfer contrast (MTC), and/or magnetization exchange (MEX). In other embodiments, CEST detects a quantity of glycosaminoglycans (GAGs). In other embodiments, pH measurement of T1 rho detects a quantity of GAGs. In other embodiments, MTC detects a quantity of collagen. In other embodiments, MEX detects a quantity of collagen and/or osteoid. In other embodiments, the microfluidic device further includes one or more channels for loading of a control sample. In other embodiments, detecting the pulse sequence signal intensity further includes comparison of the quantity of detected pulse sequence signal intensity with one or more control samples. In other embodiments, the method includes further culturing of stem cells in the microfluidic device. In other embodiments, the method includes further culturing cartilage, tendon/ligament, nucleus pulposus, annulus fibrosus, chondrocytes, tenocytes, fibroblasts, and/or notochordal cells in the microfluidic device. In other embodiments, the method includes further detection of pulse sequence signal intensity.

In one embodiment, the invention provides a method of osteogenic differentiation comprising a) seeding mesenchymal stem cells (MSCs) on a laminin-coated porous flexible membrane in an microfluidic device in culture medium in the absence of Bone Morphogenetic Protein-2 (BMP2) and the absence of flow until the MSCs attach to the membrane, b) flowing the culture medium in the absence of BMP2 such that the MSCs proliferate to produce confluent MSCs, and c) contacting the confluent MSCs with osteogenic medium containing BMP2 to produce differentiated cells that express one or more osteogenic markers exemplified by, but not limited to, osteocalcin, bone sialoprotein (bsp), osteopontin (opn), and collagen type 1. (Examples 9-13 and FIGS. 5-8).

The invention's systems and methods have several advantages. The Bone-chip (exemplified in FIG. 5) provides a platform for optical imaging of the cells and potentially biomechanical forces can be applied. The cell response to those forces can be tested in vitro without the need to harvest them. Furthermore, the chips are composed of a membrane that may be coated covalently or non-covalently with any desired ECM components allowing recapitulation of cells natural environment. Additional prominent advantage is the ability to control and to manipulate the flow sensed by cells, which has a known effect on cell differentiation as shown in several models.

The invention's systems and methods additionally have the advantage that the optical imaging can be used not only for regenerative medicine oriented research, but also to metabolism research and to disease modeling by using any of the wide range of commercially available probes for hypoxia, metabolism, inflammation and so on. The genetic tagging by the luciferase transgene can be used as a reporter to virtually any gene, including prokaryotic genes.

The invention's systems and methods also have the advantage of being able to be further developed to mimic the regenerating bone in finer ways; the chip can be used to mimic the biomechanical shears forces that are often exerted on healing fracture, using vacuum channels created parallel to the main cell culture channels. Different bone ECM components may be used. The flow can be used to introduce the system with chemokines that are known to play critical role in in-vivo fracture healing, such as TNF-alpha and IL-17, or systemically administered osteogenic therapies such as Parathyroid hormone. The outflow can be collected and analyzed for the cell secretome. A refined design of the chip may evolve in to organoid-like 3D chip. The invention's systems and methods may be used to study the relation of regenerating bone to adjacent tissues including tendon and cartilage. To sum, the invention's system and methods have a great potential to expedite the discovery and exploration of cutting edge approaches to bone tissue disease and regeneration, using methods of non-invasive imaging.

In one embodiment, the differentiated cells express a higher level of at least one of osteocalcin, bone sialoprotein (bsp), osteopontin (opn), and collagen type 1 compared to the MSCs. For example, gene expression and immunofluorescence data herein (Examples 11-13 and FIGS. 7-8) show that all three Osteopontin (OPN), Collagen type 1 and Bone Sialoprotein (BSP) genes were elevated in the static culture to 1-2 times comparing to non-differentiating cells, while in the flow cultured cells the OPN expression was tripled, the BSP expression raised by factor 5 and the Collagen-1 expression was increased by factor 6 compared to non-differentiating MSCs. The immunofluorescence data (Example 13 and FIG. 4) also show increased expression of Osteocalcin, BSP, and Collagen type 1 compared to null expression in the control MSCs.

Figure 7:
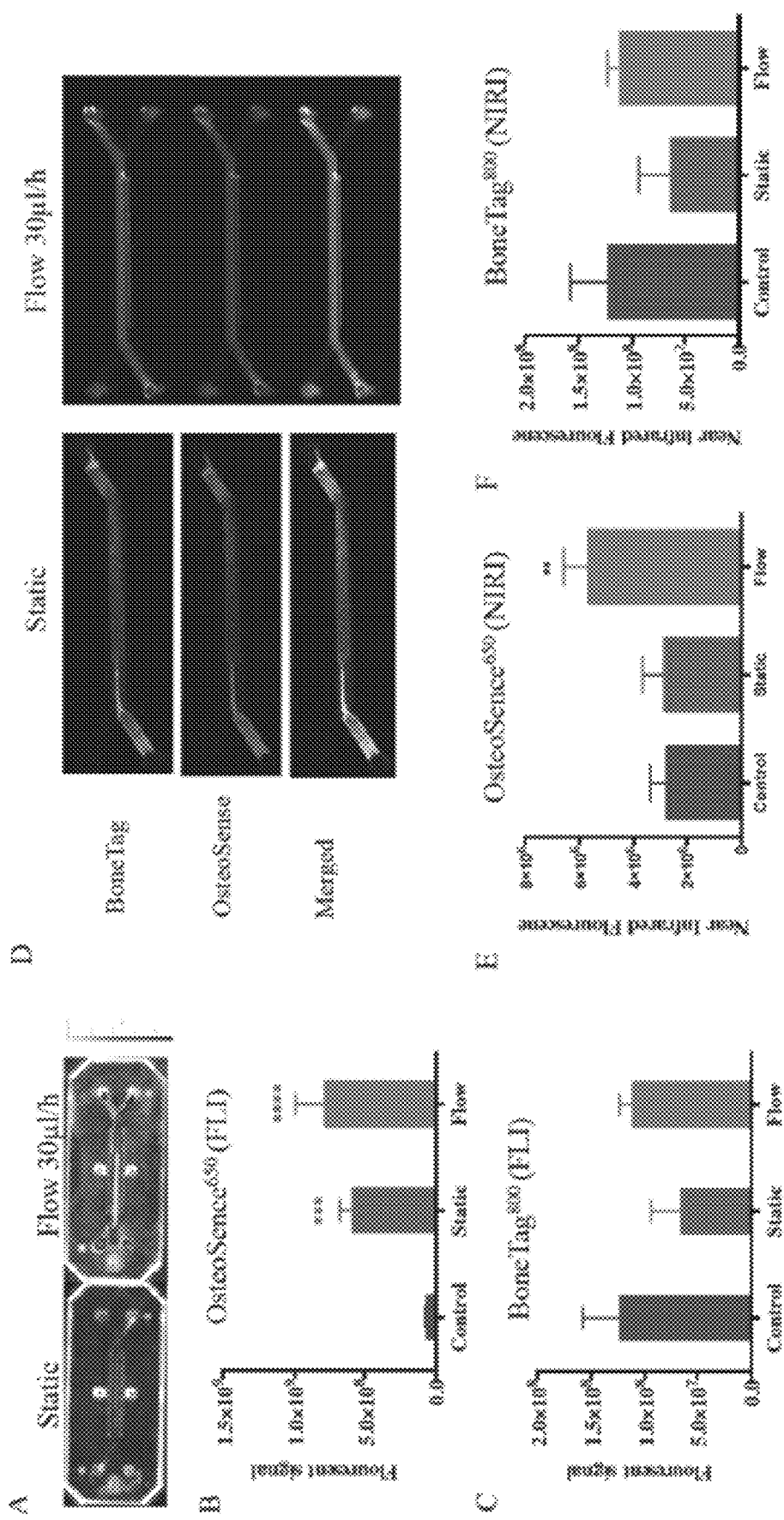
FIG. 7. Live-monitoring of MSCs osteogenic differentiation on a Bone-Chip. The differentiation was evaluated three weeks after seeding with OSTEOSENSE$^{650}$™ (fluorescent imaging agent) and BONETAG$^{800}$™ (fluorescent imaging agent) probes, that were added to the media for 24 h and washed off prior to imaging performed using two different imaging systems; fluorescent imaging system (A), the labeling was quantified using IVIS® (in vivo imaging fluorescence and bioluminescence imaging) (B&C for OSTEOSENSE$^{650}$™ (fluorescent imaging agent) and BONETAG$^{800}$™ (fluorescent imaging agent), respectively. n=5, *p<0.05; ***P<0.001 Bars indicate standard deviation), and Near Infrared imaging system (D, NIRI performed using Odyssey® CLx, Li-Cor), which allowed quantification as well (n=5, *p<0.05; ***P<0.001 Bars indicate standard deviation).
Figure 8:
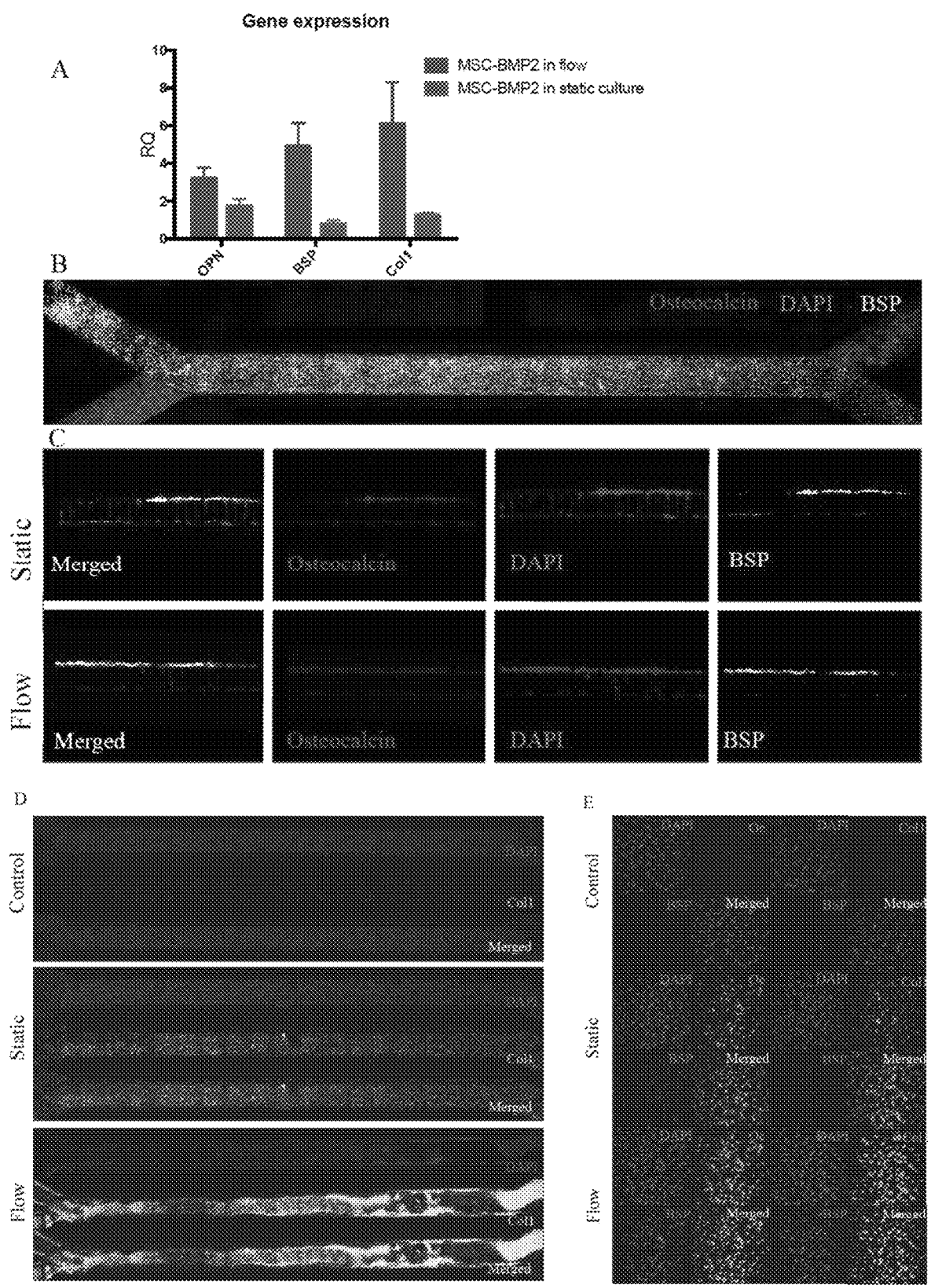
FIG. 8. Validation of MSC-BMP2 differentiation in a Bone Chip. Gene expression of the osteogenic markers Osteopontin (OPN), Bone-sialoprotin (BSP) and Collagen-1 (Col1) was evaluated 3 weeks after seeding using qRT-PCR (A, n=5, *p<0.05; Bars indicate standard deviation). The cells were fixed and fluorescently stained against the osteogenic markers Osteocalcin and BSP in the whole chips, and imaged in 10× magnification (B). Other Bone-Chips were sectioned using vibratome across the channels, stained for the same markers (C). Whole chips were stained for Col1 and the entire chip was imaged using confocal microscopy (D). In other sample set staining was performed against Osteocalcin (Oc), BSP and Col1 (E).

While not intending to limit the culture conditions, in one embodiment, the contacting step is in the presence of flow of the osteogenic medium. For example, data herein in Examples 12-13 and FIG. 8 show that all three Osteopontin (OPN), Collagen type 1 and Bone Sialoprotein (BSP) genes were elevated in the flow conditions, i.e., the OPN expression was tripled, the BSP expression raised by factor 5 and the Collagen-1 expression was increased by factor 6 compared to non-differentiating MSCs. In one embodiment, the contacting step is in the absence of flow of the osteogenic medium. For example, data herein in Examples 11-13 and FIGS. 7-8 show osteogenic differentiation of the MSC-BMP2 cells in static conditions produced 1-2 times overexpression of Osteopontin (OPN), Collagen type 1 and Bone Sialoprotein (BSP) in all differentiated cells comparing to non-differentiating cells. In one embodiment, the differentiated cells express a higher level of at least one of osteocalcin, bone sialoprotein (bsp), osteopontin (opn), and collagen type 1 in the presence of flow of the osteogenic medium compared to in the absence of flow of the osteogenic medium (Examples 11-13 and FIGS. 7-8).

Without intending to limit the type or nature of the components in the osteogenic medium, in one embodiment, the osteogenic medium contains glycerophosphate and L-Ascorbic acid. Data in Example 9 shows the exemplary use of a combination of 10 mM β glycerophosphate, 50 ng L-Ascorbic acid. In one embodiment, the β glycerophosphate concentration may range from 0.1 mM to 1.0 M, including from 0.1 mM to 1 mM, 0.1 mM to 10 mM, and 0.1 mM to 100 mM. In one embodiment, the L-Ascorbic acid amount may range from 1 µg to 10 µg, 1 µg to 50 µg, 1 µg to 100 µg, 1 µg to 500 µg, 1 µg to 1 mg, and 1 µg to 5 mg.

While not intending to limit the invention's methods to a particular method of determining the status of cells in the microfluidic device, in one embodiment, the method includes non-invasive determination of one or more of the survival status, proliferation status, and differentiation status of the MSCs and/or differentiated cells in the microfluidic device (Examples 9-13).

Data herein (Examples 9-13) demonstrate the development of a Bone-Chip for determining osteogenic differentiation in-vitro, coupled with a novel optical imaging approach which addresses the prior art's limitations while allowing the application of biomechanical forces.

Data herein (Examples 9-13) demonstrate that optical imaging can be utilized to non-invasively monitor stem cell survival and differentiation while cultured in an "organ-on-chip" device. Furthermore, the data demonstrate that the micro-engineered environment within the Bone-Chip promotes cell proliferation and more efficient osteogenic differentiation and that optical imaging can be utilized to non-invasively monitor stem cell survival and differentiation while cultured in an "Organ-on-Chip" system.

Data herein (Examples 9-13) demonstrate that optical imaging can be utilized to non-invasively monitor stem cell survival and differentiation while cultured in an "Organ-on-Chip" system, and that the micro-engineered environment within the Bone-Chip promotes cell proliferation and more efficient osteogenic differentiation. The invention was exemplified herein (Examples 9-13) using Mesenchymal Stem Cell (MSC) line over-expressing Bone Morphogenetic Protein-2 (BMP-2) under Tet-Off system and Luciferase reporter gene under constitutive promoter, that were seeded on laminin coated Chips and supplemented with osteogenic medium. Flow of media was started 24 hours after seeding, while static cultures were performed using media reservoirs. The invention's methods provide an improvement over prior methods in which it was shown that microfluidic flow can be used to pattern osteogenic differentiation of MSC bearing the Tet-off-BMP-2, by patterning the delivery of BMP-2 modulator doxycycline, although osteogenesis was demonstrated only by using imaging techniques that require termination of the culture— ALP and Von Kossa stainings, calcium deposition measurement and immunohistochemistry against Bone-sialoprotein.

Data herein (Examples 9-13) demonstrate cell survival/proliferation of cells grown on the Bone-Chips under constant flow of media was enhanced comparing to the cells grown in static conditions; Luciferase reporter gene expression and activity, reflecting the cell survival and proliferation, was quantified using bioluminescence imaging twice a week and significant advantage to the flow system was observed. Also, the micro-engineered environment with flow had positive effect on osteogenic differentiation, when compared with static cultures. Fluorescent imaging was performed using the osteogenic ECM-targeted probes OSTEOSENSE$^{650\text{TM}}$ (fluorescent imaging agent) and BONETAG$^{800\text{TM}}$ (fluorescent imaging agent), followed by quantification which showed higher osteogenic differentiation of the cells under the flow conditions. Gene expression analysis confirmed the osteogenic differentiation of the MSC-BMP2 cells, showing upregulation of Osteopontin, Collagen type 1 and Bone Sialoprotein (BSP) in all cells, yet higher expression was observed in the cells cultured in flow conditions. Immunofluorescent staining performed against the Osteocalcin, Col1, and BSP markers on transverse sections across the channels or whole Bone-Chips illustrated robust osteogenesis in the flow culture and lessened differentiation in the static culture. To sum, the Bone-Chip allows monitoring cell survival, proliferation and osteogenic differentiation in-vitro using optical imaging, without the need for sacrificing the Chips enabling additional endpoints or culture time.

More particularly, data herein (Examples 9-13) focused on the longitudinal non-terminal imaging of a "Bone-on-a-chip" system. For this purpose, a differentiating system that includes Mesenchymal Stem Cells (MSCs) over-expressing of Bone Morphogenetic Protein-2 (BMP-2) was utilized. The recombinant BMP-2 protein is FDA-approved and in wide use in the clinical settings using a very high dose which quickly deteriorates, while different experimental systems offer sustained expression of a milder dose for as long as 14 days using non-viral gene delivery, or for the cell life time in case of MSCs transfected with lentivirus. BMP-2 affects MSC via both by paracrine and autocrine signaling, that are transduced to the nucleus via secondary messengers including the Smad family which enhance the expression of osteogenic transcription factors such as RUNX2, Osterix and others. To allow a controllable expression of BMP-2 in MSC, the invention used the exemplary Tetracycline-off system, that was successfully examined in a various of clinically relevant models including spinal fusion, long-bone allograft regeneration, radial defects, and more.

Figure 6:
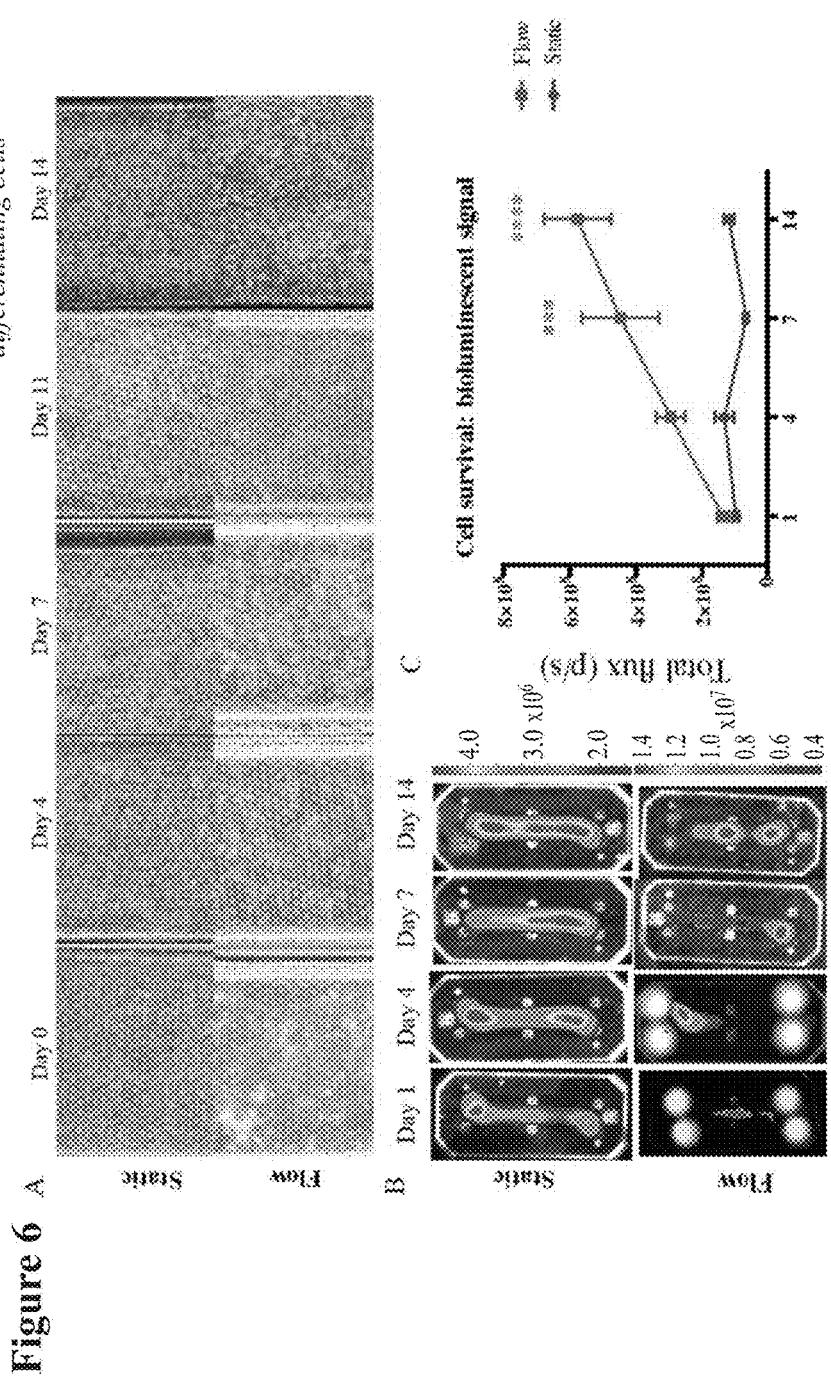
FIG. 6. Cell survival and proliferation on the Bone-Chip. Micrographs of the cells in the Bone-Chip grown for 2 weeks were taken biweekly, in osteogenic conditions with or without flow. (A). Bioluminescent images taken on the same time points using IVIS® (in vivo imaging fluorescence and bioluminescence imaging) imager. The images are relative and the scale of the color code is depicted on the right side of each group(B). Quantitative analysis of total BLI imaging that was done for two weeks (C, bars indicate SD, n=5, *p<0.01; **P<0.001).

Data herein demonstrate that BLI of cells continuously expressing the luciferase gene can faithfully reflect cell proliferation, and detect superior proliferation when it was present under the flow conditions (FIG. 6). Next, FLI and a targeted molecular probe were used to allow detection of osteogenic differentiation, signified by osteogenic ECM secretion (FIG. 7). Data herein show that the osteoid-targeted OSTEOSENSE$^{650TM}$ (fluorescent imaging agent) probe provided the ability to monitor osteogenesis and even discern more rigorous differentiation comparing to moderate differentiation, as confirmed by gene expression analysis and immunofluorescence (FIG. 8). The BONETAG$^{800TM}$ (fluorescent imaging agent) which serves as a calcium chelator could not be used to produce meaningful data, yet it might be used for cultures sustained for longer periods when the culture is expected to mature. Another interesting observation was that the IVIS® (in vivo imaging fluorescence and bioluminescence imaging) system, originally designated to rodent imaging, could detect the differentiation towards the osteoblastic lineage but did not contribute to the characterization of which. Only the combined used of the IVIS® (in vivo imaging fluorescence and bioluminescence imaging) system and the NIR imager, conceived to read out smaller samples such as western blot gels, has assembled a finer image of the differentiation process. Thus, data herein show that the IVIS® (in vivo imaging fluorescence and bioluminescence imaging) can be used in invention's system to answer a yes/no question: is there any differentiation? While the NIR imager can be used to answer a more delicate question: what's the extent of the desired differentiation?

Organ-on-chip system allows monitoring of the cell survival and proliferation in vitro using BLI imaging system and monitor the osteogenic differentiation of the cell on the chip in real time, without the need of harvesting the cells and disrupting the culture conditions. Here, the Inventors demonstrate that the flow conditions affect both proliferation and the differentiation of the MSCs that overexpress BMP2.

I. Open-Top Microfluidic Devices.

The invention contemplates fluidic devices including one or more osteogenic cell types. Accordingly, the present invention contemplates the use of open-top microfluidic devices, exemplified in FIGS. 10-12. Open-top microfluidic devices include but are not limited to microfluidic devices having removable covers, such as removable plastic covers, paraffin covers, tape covers, etc.

Many of the problems associated with earlier systems can be solved by providing an open-top style microfluidic device that allows topical access to one or more parts of the device or cells that it includes. For example, the microfluidic device can include a removable cover, that when removed, provides access to the cells of interest in the microfluidic device. In some aspects, the microfluidic devices include systems that constrain fluids, cells, or biological components to desired area(s). The improved systems provide for more versatile manipulations using microfluidic devices, including improved application of treatments being tested, improved seeding of additional cells, and/or improved aerosol delivery for select tissue types.

Therefore, in one embodiment, the present invention contemplates using a microfluidic device with an opening that provides direct access to device regions or components (e.g. access to a 2D or 3D matrix (such as 2D or 3D extracellular matrix) containing cultured and/or differentiated cells, access to one or more cellular components, etc.). Although FIGS. 10-12 provide an embodiment wherein the opening is at the top of the device (referred to herein with the term "open-top"), the present invention contemplates other embodiments where the opening is in another position on the device. For example, in one embodiment, the opening is on the bottom of the device. In another embodiment, the opening is on one or more of the sides of the device. In another embodiment, there is a combination of openings (e.g. top and sides, top and bottom, bottom and side, etc.).

While detailed discussion of the "open-top" embodiment is provided herein, those of ordinary skill in the art will appreciate that many aspects of the "open-top" embodiment apply similarly to open bottom embodiments, as well as open side embodiments or embodiments with openings in any other regions or directions, or combinations thereof. Similarly, the device need not remain "open" throughout its use; rather, as several embodiments described herein illustrate, the device may further comprise a cover or seal, which may be affixed reversibly or irreversibly. For example, removal of a removable cover creates an opening, while placement of the cover back on the device closes the device. The opening, and in particular the opening at the top, provides a number of advantages, for example, allowing (i) the creation of one or more 3D ECM layers for simulating the application of topical treatments on the cells, tissues, or organs, or (ii) the addition of chemical or biological components such as the seeding of additional cell types for simulated tissue and organ systems.

The present invention contemplates a variety of uses for these open-top microfluidic devices and methods described herein. In one embodiment, the present invention contemplates a method of topically administering an agent (whether a drug, food, gas, or other substance) including 1) providing a) an agent and b) microfluidic device including i) a chamber, said chamber including a lumen and projections into the lumen, said lumen including ii) a 3D matrix (in some embodiments a 3D ECM) anchored by said projections and including cell in, on or under said 3D matrix, said matrix positioned above iii) a porous membrane and under iv) a removable cover, said membrane in contact with v) fluidic channels; 2) removing said removable cover; and 3) topically contacting said cells in, on or under said matrix with said agent. These uses may apply to the open-top microfluidic devices described below and herein.

A. Open-Top Microfluidic Devices without Extracellular Matrix (ECM).

In one embodiment, open-top microfluidic devices do not contain ECM, either as a 3D ECM or a 2D ECM layer. Thus, the present invention also contemplates, in one embodiment, a layered structure including i) fluidic channels covered by ii) a porous membrane, said membrane including iii) a layer of cells and said membrane positioned below said cells. In one embodiment, there is a removable cover over the cells.

Additional embodiments are described herein that may be incorporated into open-top microfluidic devices without a three dimensional matrix such as an extracellular matrix (3D ECM)s.

B. Open-Top Microfluidic Devices with Extracellular Matrix (ECM).

In one embodiment, open-top microfluidic devices contain a matrix such as an ECM, as a 2D or 3D layer. In one embodiment, the open-top microfluidic device has an open-top region that reduces the impact of stress that can cause the delamination of tissue or related component(s) (e.g., such as a three dimensional extracellular matrix (3D ECM)). Thus, in one embodiment, the open-top microfluidic device includes a matrix including, but not limited to a 3D ECM. In one embodiment, the open-top microfluidic device does not contain a 3D ECM.

The present invention also contemplates, in one embodiment, a layered structure including i) fluidic channels covered by ii) a porous membrane, said membrane including iii) a layer of cells and said membrane positioned below iv) a 3D ECM. In one embodiment, there is a removable cover over the 3D ECM (and/or cells). It is not intended that the present invention be limited to embodiments with only one 3D ECM. In one embodiment, the layered structure further includes a second 3D ECM (e.g. positioned under said membrane). The 3D ECM(s) or coatings can be patterned or not patterned. Moreover, when patterned, the pattern need not extend to the entire surface. For example, in one embodiment, at least a portion of said 3D ECM is patterned. It is not intended that the present invention be limited by the nature or components of the 3D ECM or ECM coating. A variety of thickness is contemplated. In one embodiment of the layered structure, said 3D ECM is between 0.2 and 6 mm in thickness.

In one embodiment, the present invention contemplates an open-top microfluidic device, exemplified by those described in WO2017096297, published Jun. 8, 2017, incorporated herein by reference.

The various methods and techniques described herein provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are sources of mesenchymal stem cells, osteoblasts, bone cells or stem cells, seeding and culturing on a microfluidic device, imaging methods, including labeling and detection, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the herein-described elements in all possible variations thereof is encompassed by the invention unless otherwise indicated herein or otherwise clearly contradicted by context.

Furthermore, numerous references have been made to patents and printed publications throughout this specification. Each of the references and printed publications cited herein are herein individually incorporated by reference in their entirety.

It is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

Example 1

Micro Imaging for Non Invasive Monitoring of Stem Cell-Induced Mineralization

Mesenchymal stem cells (MSCs) can differentiate to various skeletal cells including osteoblasts. A common assay of MSC differentiation to osteogenic cells includes measurements of mineralization within the culture. Several methods can be used to monitor mineralization over time in chips Example 2

Labeling Agents for Stem Cell-Induced Mineralization

Fluorescence imaging—bisphosphonate imaging probes such as OSTEOSENSE™ (fluorescent imaging agent) (Perkin Elmer) can be added to the chip at different time points, washed and then the chip is imaged in an optical scanner. Hydroxyapatite (HA) is a mineral form of calcium apatite and is the major mineral product of osteoblasts. Therefore, HA levels are a good biomarker for osteoblast activity. In addition, abnormal accumulation of HA can be indicative of a disease state. OSTEOSENSE™ (fluorescent imaging agent) imaging agents bind with high affinity to HA. Since hydroxyapatite (HA) is known to bind pyrophosphonates and phosphonates as well as synthetic bisphosphonates with high affinity, OSTEOSENSE™ (fluorescent imaging agent) agents were designed as bisphosphonate imaging agents. These probes consist of a pamidronate backbone functionalized with near-infrared fluorophore off the amino terminus of the R2 side chain. Specifically, OSTEOSENSE™ (fluorescent imaging agent) imaging agents can be used to image areas of microcalcifications, bone remodeling and enables imaging of bone growth and resorption. The bisphosphonate probe attaches to micro calcifications and the fluorescent readout provides quantification of mineralization.

Example 3

Other Labeling Agents for Stem Cell-Induced Mineralization

Bisphosphonates (BPs; also known as diphosphonates), such as methylene diphosphonate (MDP) and zoledronic acid, can be labeled with technetium-99m ([99mTc]-BPs) for use in bone scintigraphy as has been used to detect osteoporosis and other skeletal-related events (SREs). These chemicals bind hydroxyapatite, which allow for imaging of bisphosphonates as described above. [18F]-Fluoride is another nuclide that is commonly used for bone imaging, and positron emission tomography (PET) and is believed to be superior to [99mTc]-BPs for the diagnosis of SREs.

Micro SPECT/PET imaging-99mTc-Methyl diphosphonate (Tc-MDP) can be added to the chip at different time points, washed and then the chip is imaged using a micro SPECT scanner. Alternative probes are ['8F)-Fluoride or 68Ga-Labeled (4-{[(bis(phosphonomethyl))carbamoyl]methyl}-7,1 O-bis(carboxymethyl)-I,4, 7, I 0-tetraazacyclododec-1-yl)acetic acid (BPAMD) [68Ga]BPAMD that can be imaged using a micro PET scanner. These probes also attach to mineralization foci and the uptake readouts can provide quantitative data of mineralization.

Example 4

Micro Imaging for Non Invasive Monitoring of Stem Cell-Induced Mineralization

Micro CT-high-resolution micro CT scanners can detect mineral particles as small as 500 nm. A non-destructive scan of the chip can provide an accurate measurement of mineralization generated by the developing tissues.

Example 5

Micro Imaging for Non Invasive Monitoring of Extracellular Macromolecules Secreted by Stem Cells Different types of stem cells including MSCs and induced pluripotent stem cells (iPSCs) have been shown to differentiate to joint tissue cells such as osteoblasts, osteocytes, chondrocytes, tenocytes, fibroblasts, notochordal cells, and/or nucleus pulposus cells. While differentiating, the cells secret characteristic extracellular molecules such as aggrecan, glycosaminoglycans (GAGs), collagens and more.

A way to monitor the secretion of these molecules in a chip will include the use of micro MRI using different pulse sequences, including but not limited to: chemical exchange saturation transfer (CEST)—GAGs measurement; pH measurement Tl rho—GAGs measurement, magnetization transfer contrast (MTC)—collagen measurement, magnetization exchange (MEX)—collagen and osteoid measurement.

Chemical exchange saturation transfer (CEST) also provides the ability to analyze the GAG content in cartilage. The most common method for acquisition of a CEST data set is to acquire multiple image data sets with presaturation at different offset frequencies around the water resonance and one reference data set without saturation or with saturation at a very large offset frequency. The normalized signal as a function of the presaturation offset (termed the z-spectrum) can then be used to determine and quantify CEST effects, which are asymmetric with respect to the water resonance (i.e., a CEST effect appears either up- or down-field from water and therefore can be extracted from the z-spectrum via analysis of its asymmetry with respect to the water resonance). Chemical exchange saturation transfer (CEST) is a magnetic resonance imaging (MRI) contrast enhancement technique that enables indirect detection of metabolites with exchangeable protons. Endogenous metabolites with exchangeable protons including many endogenous proteins with amide protons, glycosaminoglycans (GAG), glycogen, myo-inositol (MI), glutamate (Glu), creatine (Cr) and several others have been identified as potential in vivo endogenous CEST agents. These endogenous CEST agents can be exploited as non-invasive and non-ionizing biomarkers of disease diagnosis and treatment monitoring.

Magnetization Transfer Contrast (MTC) MM is an imaging method that evolved from NMR spectroscopy. In tissue imaging, MTC relies upon the interaction of less mobile protons associated with macromolecules such as proteins and their interactions with protons freely associated with water. The premise is that in a system where molecules move and exchange position, whether it be a change in spatial position in asymmetrical molecules or an exchangeable proton between a molecule and water, the magnetization state will also move and be transferred.

A two pool model can be utilized to illustrate the theory behind MTC MRI. Conventional MRI detects only the free water pool while the macromolecular pool remains mostly undetected. Both the macromolecular and free water pools are centered around the same frequency but the macromolecular pool is shallower and wider. Saturation is achieved by applying an off-resonance radio frequency (RF) pulse specific to a peak in the macromolecular pool before excitation at the center frequency. The RF pulse saturates the signal from the section leading to ideally no signal at the off-resonance frequency. Since both pools interact this saturation is transferred to the free water pool. While it is not possible to detect the changes in the macromolecular pool directly, it can be assumed that the loss in signal intensity of the free water pool corresponds to the changes in the macromolecular pool.

Ideally, an increase is preferable to a decrease in signal intensity since it is easier to visualize changes in brightness over changes in darkness. To achieve this type of image, a Magnetization Transfer Ratio (MTR) is calculated using a base image without saturation to measure the relative loss of signal intensity in a pixel by pixel basis: MTR=Nonsaturated-Saturated/Nonsaturated. MTC is very similar in function to CEST. CEST focuses on a limited part of magnetization transfer by linking it to chemical exchange systems.

Quantitative magnetization transfer (qMT) imaging is MR technique which utilizes a two-pool model of magnetization exchange to acquire information regarding the cartilage macromolecular matrix. qMT imaging techniques typically require multiple MT-contrast images with different magnetization preparatory pulses resulting in long scan times which have limited cartilage assessment to ex-vivo specimens. Cross-relaxation imaging (CRI) is a qMT method which can create three-dimensional parametric maps of articular cartilage measuring the fraction of macromolecular bound protons (f), the exchange rate constant between macromolecular bound protons and free water protons (k), and the T2 relaxation time of macromolecular bound protons (T2B) with high resolution and relatively short scan time based upon a limited number of MT-contrast images. The parameter f provides an indirect measure of macromolecular content, while the parameters k, and T2B reflect the efficiency of magnetization exchange between macromolecular bound protons and free water protons and the spin diffusion between proton sites in macromolecules respectively which may be influenced by macromolecular organization and ultra-structure Example 6

Micro Imaging for Non Invasive Monitoring of Osteogenic Cells-On-Chip

Microfluidic culture devices are attractive systems to model physiological and pathological conditions of tissues and organs. Although these devices allow fluorescent and light microcopy imaging of cultured cells, one of its current limitations is that various types of analyses require sacrificing of the culture. The Inventors have previously utilized micro imaging systems to monitor stem cell differentiation in ex-vivo 3D tissue constructs.

Of interest is utilizing optical imaging to non-invasively monitor stem cell survival and differentiation while cultured in an "organ-on-chip" device. Stiffer membrane and microfluidic environment will promote more efficient osteogenic differentiation.

To explore this possibility, the organ-on-chip was coated with ECM crosslinked with UV prior to cell seeding. Then mesenchymal stem cell line overexpressing BMP2 and Luciferase reporter genes were seeded on the coated organ-on-a-chip (see dimensions and the set up for microfluidic studies in FIG. 1 and supplemented with osteogenic media. The static cultures were performed using 200 µl media reservoirs that were changed every other day. The flow studies were performed using 30 µl/l flow of media pulled through using specialized pump (FIG. 1). Micrographs were taken twice a week and survival of the cells was monitored using bioluminescent imaging. The media was changed to media with Luciferin and imagined using IVIS® (in vivo imaging fluorescence and bioluminescence imaging) (Perkin Elmer). The osteogenic differentiation after 3 weeks of culture in osteogenic media was monitored using florescent probes OSTEOSENSE$^{650}$™ (fluorescent imaging agent) and BONETAG$^{800}$™ (fluorescent imaging agent) that were introduced 24 hours before the imaging and were imaged using fluorescent imaging (FLI) and near infrared (NIR) imaging, confocal microscopy and immunostaining.

Example 7

Monitoring Cell Proliferation without Harvest or Culture Disruption

A comparison of chips grown in static culture condition to chips grown under constant flow of media (30 µl/l) was performed along with evaluation of the effect of the flow on cell survival/proliferation of cells and the extent of osteogenic differentiation. The microscopic images (FIG. 1A) show proliferation of the cells under the flow conditions, however it is difficult to quantify the extent of proliferation using this method without disrupting the cultures. Therefore, the Inventors used cell that express Luciferase reporter gene and the cell proliferation was quantified using bioluminescent imaging (BLI) twice a week (FIG. 2B, C). This imaging method allowed monitor the proliferation of the cells without the need to harvest or disrupt the culture and significant advantage to the flow system was observed. Also microfluidic environment had positive effect on osteogenic differentiation, when compared with static cultures.

Figure 3:
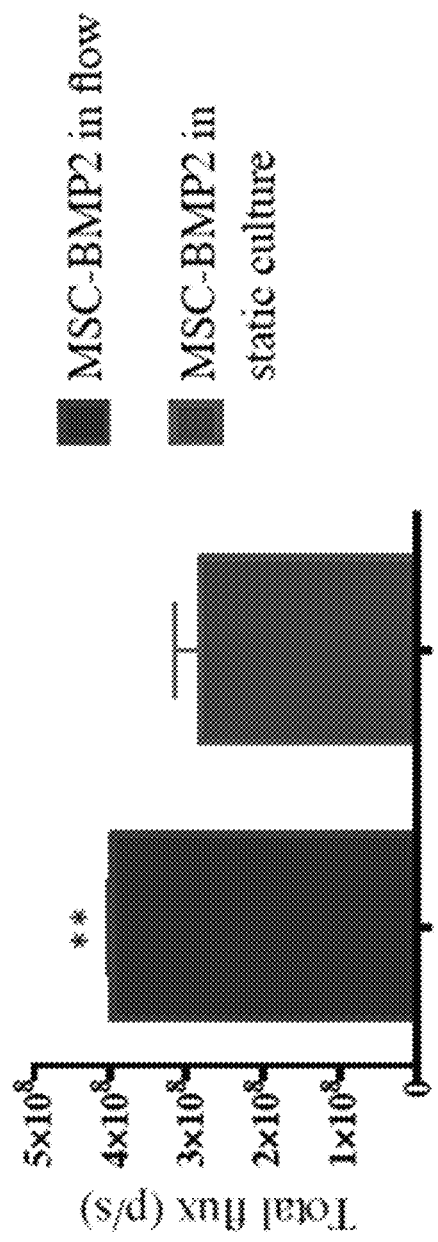
FIG. 3. Osteogenic differentiation at Week 3 measured with two probes (OSTEOSENSE™ (fluorescent imaging agent) and BONETAG™ (fluorescent imaging agent)) using two different imaging systems: fluorescent imaging system (IVIS® (in vivo imaging fluorescence and bioluminescence imaging), Perkin Elmer) and Near Infrared imaging system (Odyssey® CLx, Li-Cor).
Figure 3:
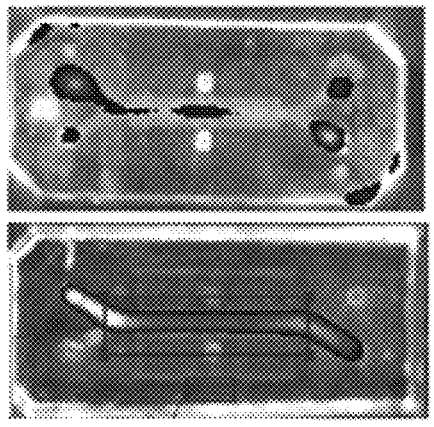
Figures 3, 3C:
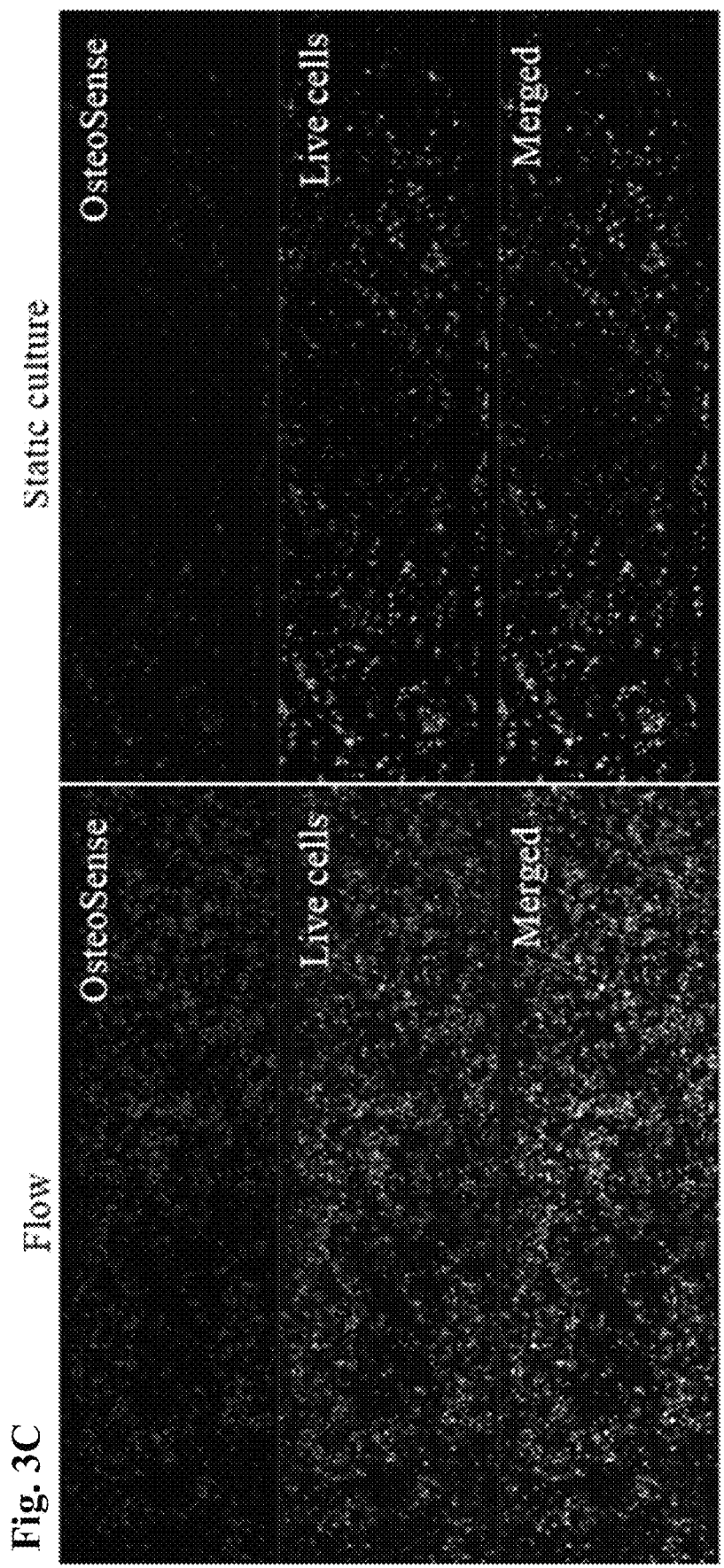

This effect was observed in fluorescent imaging of osteogenic differentiation probes using two different systems—FLI and Near Infrared (FIG. 3). The probes can be detected using different wavelengths of fluorescence, therefore both probes can be added simultaneously and imaged separately. The quantification of FLI (FIG. 3A, B) of BONETAG™ (fluorescent imaging agent) showed higher osteogenic differentiation of the cell under the flow conditions. OSTEOSENSE™ (fluorescent imaging agent) was also imaged using confocal microscopy in conjugation with Live/Dead staining (FIG. 3C) showing that most of the live cells absorbed OSTEOSENSE™ (fluorescent imaging agent) probe and again the flow chips were stained in more efficiently than the static cultures. The NIR system is considered more sensitive and the quantification of the image more accurate. Here, the Inventors demonstrate that they system is capable of detecting the same trend using both probes (FIG. 3D).

Example 8

Confirmation of Osteogenic Differentiation

Figure 4:
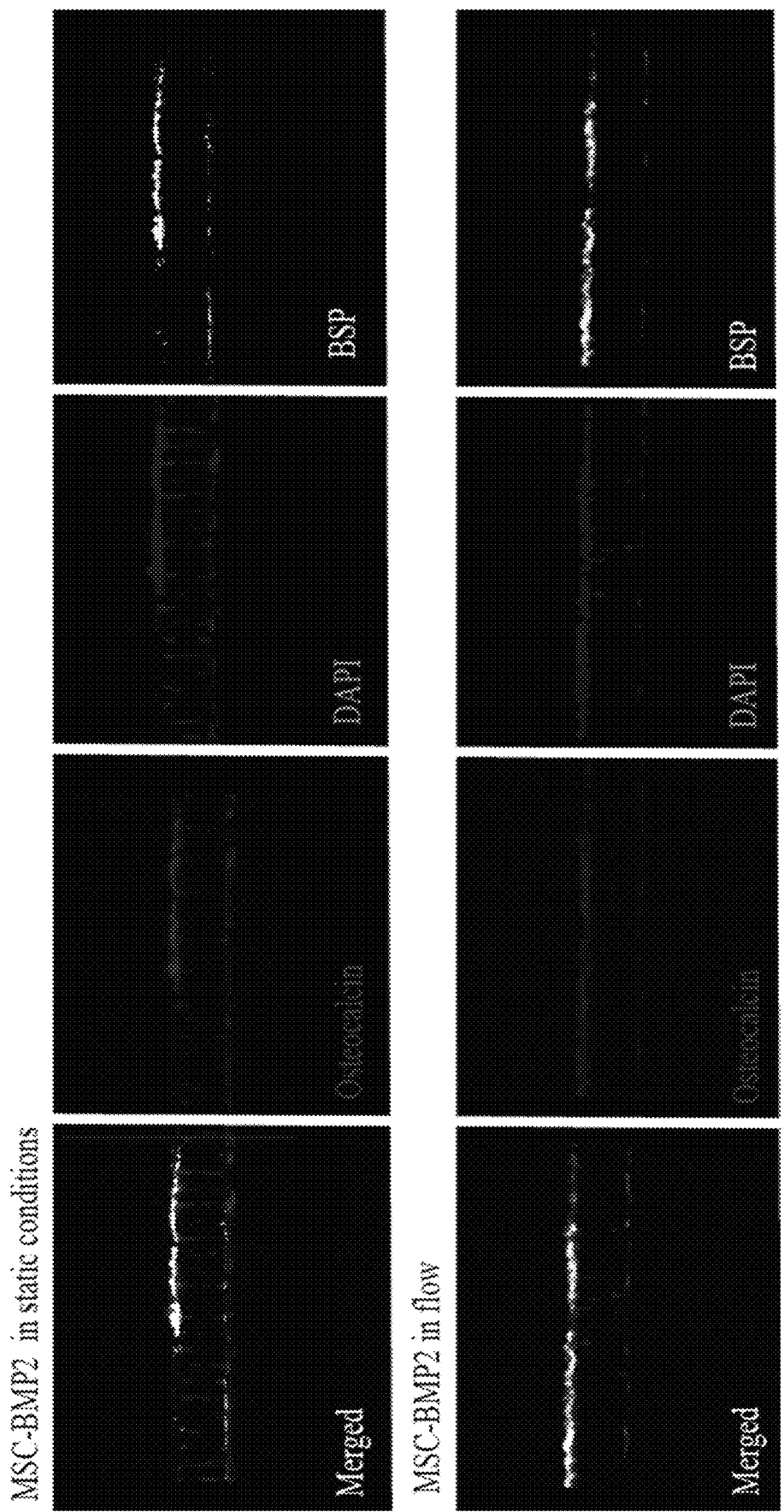
FIG. 4. Immunostaining of osteogenic differentiation of MSC-BMP2 in Organ-on-chip. The chips were sectioned using vibratome across the channels. The sections were stained using with immunofluorescent staining against the osteogenic markers osteocalcin and bone sialoprotein (BSP), and imaged using confocal microscopy.
Figure 5:
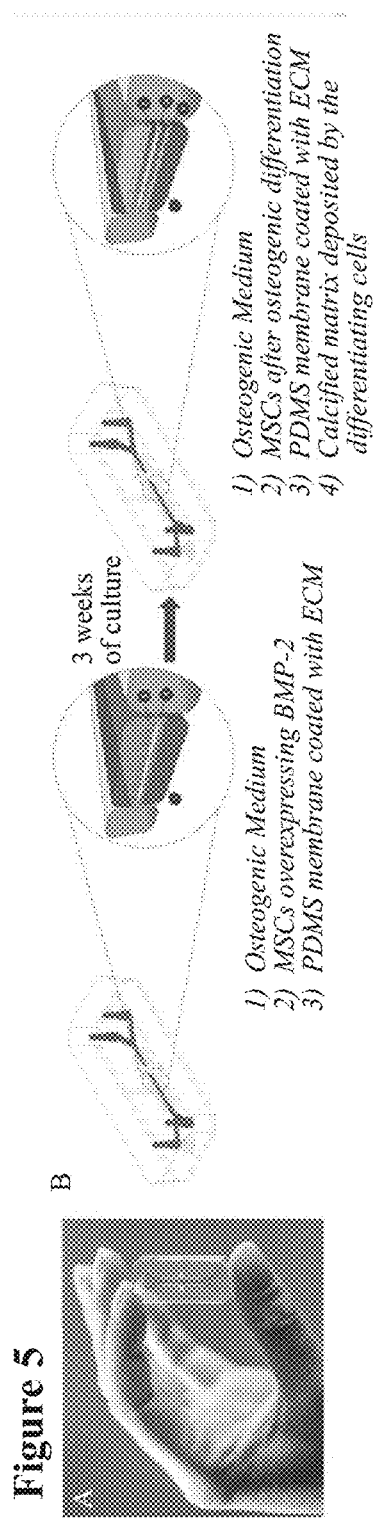
FIG. 5. Image of Bone-Chip and diagram illustrating the workings of Chip. The PDMS Chip (A) contains a middle channel with a porous flexible membrane upon which the cells are seeded after coating with appropriate extracellular matrix (B).

In order to confirm osteogenic differentiation of the MSC-BMP2 cells, the harvested chips were sectioned using vibratome creating transvers sections across the channels. Then these sections were subjected to immunofluorescent staining using primary antibody against Osteocalcin and Bone Sialoprotein (BSP) osteogenic markers. The staining shows cells on both sides of the membrane in both conditions, but mainly in the top channel. In both conditions there was positive staining for both marker, indicating osteogenic differentiation, however the staining looks more prominent in the chips that were cultured in flow (FIG. 4 bottom panel).

Example 9

Methods

Generation of MSC-Tet-Off-BMP2 Cell with Constitutive Luc Reporter Gene Expression Generation of rhBMP-2 overexpressing MSCs was described previously[23]. Briefly, cells from the C3H10T1/2 MSC line were stably transfected with a ptTATop-BMP2 plasmid vector that encodes for a tetracycline transactivator and rhBMP-2 (creating a tet-off system). Using the inducible human BMP-2 expression vector, ptTATop-BMP2, the expression of hBMP-2 could be shut down by administration of doxycycline, an analogue of tetracycline, or turned on by doxycycline absence. Then, the cells were transfected with a Lenti-viral vector encoding for Luc2 reporter gene under the constitutively expressed ubiquitin promotor[22]. Cells were cultured in 100-mm culture plates in a complete growth medium (Dulbecco's modified Eagle's medium containing 10% fetal bovine serum, 2 mM L-glutamine, 100 U/mL penicillin, and 100 U/mL streptomycin (Gibco-Life Technologies, Carlsbad, CA) in a 5% CO2/95% air atmosphere at 37° C. 1 mg/mL Doxycycline was added to the medium to prevent cell differentiation before seeding onto the chips.

Bone-Chip System

Soft lithography was used to prepare the chips with polydimethylsiloxane (PDMS). The chips were then covalently coated with 50 ug/mL Laminin in PBS (Sigma), using ER1/2 cross-linker (Emulate, Inc.) and exposure to UV light [356 mm, 20 min]. Before the chip studies commenced, the cells were trypsinized and centrifuged at 300 g and 4° C. for 5 min. The cells were counted using the Trypan blue exclusion test and seeded on the coated chips in $1\times10^6$ cells/ml concentration in high glucose complete growth media supplemented with 1 µg/ml Doxycycline to prevent BMP2 expression. 50 µl of cell suspension was applied into the top channel. Dead/non-adhered cells were removed after 3-6 hours by flushing media through the device and flow was started 24 hrs after seeding at a rate 30 µl/hr of media pulled through, using a specialized pump. The static cultures were performed using 200 µl media reservoirs that were changed every other day. Once the cells reached confluence (2-3 days), the growth media was replaced by Doxycycline-deficient osteogenic media (10 mM β glycerophosphate, 50 µg L-Ascorbic acid).

Cell Growth and Viability

Micrographs were taken twice a week for two weeks using EVOS light microscopy (ThermoFisher, Waltham, MA). Cell survival was monitored biweekly using Bioluminescent Imaging (BLI); the media was changed to media supplemented with [0.126 µg/µl] Luciferin, and the BLI signal was captured immediately using Xenogen IVIS® (in vivo imaging fluorescence and bioluminescence imaging) Spectrum (PerkinElmer, Waltham, MA), 1 min exposure time. The image analysis was done using total influx data calculated on the same size ROI, normalized to background noise in each image.

Non-Invasive Osteogenic Differentiation Assessment (FLI, NIR-OSTEOSENSE$^{650}$™ (Fluorescent Imaging Agent)/BONETAG™ (Fluorescent Imaging Agent))

The osteogenic differentiation was evaluated after 3 weeks of culture in osteogenic media using florescent probes. Data herein compared tetracycline-deprived in static and flow culture, and used non-differentiating cells supplemented with tetracycline as a negative control. OSTEOSENSE$^{650}$™ (fluorescent imaging agent) (Perkin Elmar) 0.625 nmol and BONETAG$^{800}$™ (fluorescent imaging agent) (LI-COR Biosciences, Lincoln, NE) 2.56 nmol were introduced 24 hours before the imaging, and were imaged using fluorescent imaging (FLI) and near infrared imaging (NIRI) systems—using IVIS® (in vivo imaging fluorescence and bioluminescence imaging) Xenogen for the former, Odyssey® CLx Imaging System (LI-COR Biosciences) for the later.

Gene Expression Analysis

Total RNA was isolated using RNAeasy® (RNA extraction) isolation kit (Qiagen, Hilden, Germany) on week 3 of osteogenic differentiation. Single-stranded cDNA was created with the aid of a reverse transcription kit (Invitrogen) and employed as a template for real time-PCR with Taqman® (polymerase) gene expression assays using ABI7500 ® (PCR machine) Prism (Applied Biosystems, Carlsbad, CA), as previously described. Quantitative RT-PCR was performed to quantify the expression of the osteogenic genes Osteopontin (Opn), Collagen 1 (Col1) and Bone-sialoprotein (BSP). The house keeping gene 18S was used as a to normalize the data, non-differentiating cells (Day 0) were used as calibrator sample to quantify the relative gene expression (RQs).

Immunofluorescence

Four weeks after seeding, the cells were fixed for immunostaining using 4% formaldehyde. Nonspecific antigens were blocked by applying blocking serum-free solution (Dako, Santa Clara, CA). Chips were stained with primary antibodies against mouse BSP (1:100 Cat #MBS176061, MyBiosourse, San Diego, CA), Col1 (1:250 Cat #ab21286, Abcam, Cambridge, MA) and OC (1:100 Cat #PA1-85754, ThermoFisher Scientific) to examine osteogenic differentiation. The primary antibodies were applied into the chips, incubated in 4° C. overnight, and washed off using PBS; the chips were then incubated with secondary antibodies (Supplemental Table 1) for 1 hr in room temperature, after which they were washed off with PBS. The chips were then stained with 4',6-diamidino-2-phenylindole dihydrochloride (DAPI, 1 µg/ml) for 5 min in the dark, after which they were again washed 3 times with PBS. A VECTAMOUNT(mounting medium) mounting medium (Vector Laboratories, Burlingame, CA) was applied into the Bone-Chip. The chips were imaged using a 4-channel Laser Scanning Microscope 780 (Zeiss, Pleasanton, CA) with 10× magnification, z-stacking, and tile scanning. For zoom-in images, a single z-stacked image was generated using 10× magnification. All chips were scanned using the same gain and exposure settings.

Example 10

Viability

The cell proliferation of cells that were grown on the Bone-Chips that were under constant flow of media (30 µl/h) was elevated comparing to the cells grown in static conditions. The microscopic images show proliferation of the cells under both static and flow conditions, achieving 100% confluence 14 days after seeding (FIG. 6A). However, the BLI signal generated by the constitutively expressed Luciferase reporter gene, reflecting the cell survival and proliferation, demonstrated notable advantage to the flow system in qualitative analysis (FIG. 6B). Quantitative analysis showed significantly higher signal in the flow-culture group beginning a week after cell seeding (FIG. 6C). The cells in the flow chips demonstrated elevation in the measured BLI signal indicating proliferation, while the cells in the static group has yielded a constant BLI signal indicating survival, but no proliferation.

Example 11

Optical Imaging of Osteogenesis

The micro-engineered environment with flow had positive effect on osteogenic differentiation, when compared with static cultures (FIG. 7-8). This effect was observed in fluorescent imaging of osteogenic differentiation probes using two different systems— FLI and NIRI (FIG. 7). The probes can be detected using different wavelengths of fluorescence, therefore both probes could be added simultaneously and imaged separately. The quantification of FLI of OSTEOSENSE$^{650TM}$ (fluorescent imaging agent), performed three weeks after seeding, showed significantly higher osteogenic differentiation of the cells under the flow conditions, and both were significantly higher than the control, MSC-BMP2 cells in which differentiation was halted by tetracycline supplementation (FIG. 7A,B). The fluorescent signal measured in the static and the flow cultures was higher than the control, the static by significance of $P<0.05$ while the flow by significance of $P<0.001$. However, most of the live cells given BONETAG$^{800TM}$ (fluorescent imaging agent) probes produced a very low BONETAG$^{800TM}$ (fluorescent imaging agent) FLI signal, comparable to the control cells (FIG. 7C). The NIRI system is considered more sensitive and provides a more accurate quantification of signal. Data herein show that this system is capable of detecting a similar trend (FIG. 7D); the OSTEOSENSE$^{650TM}$ (fluorescent imaging agent) signal detected by NIRI was significantly higher in the flow culture comparing to both static culture and control (FIG. 7E), while the use of BONETAG$^{800TM}$ (fluorescent imaging agent) probe did not produced signal higher than the control using both imaging systems (FIG. 7F).

Example 12

Gene Expression

The gene expression analysis, performed after three weeks of culture in osteogenic media to validate the findings obtained by imaging methods. The analysis confirmed the osteogenic differentiation of the MSC-BMP2 cells in both static and flow conditions, showing overexpression of Osteopontin (OPN), Collagen type 1 and Bone Sialoprotein (BSP) in all cells, but significantly higher expression of all the genes was observed in the cells cultured in flow conditions comparing to static culture (FIG. 8A). All three examined genes were elevated in the static culture to 1-2 times comparing to non-differentiating cells, while in the flow cultured cells the OPN expression was tripled, the BSP expression raised by factor 5 and the Collagen-1 expression was increased by factor 6.

Example 13

Immunofluorescence

To further affirm the imaging results, immunofluorescent staining was performed against the Osteocalcin and BSP markers on whole Bone-Chips (FIG. 8B) and transverse sections across the channels (FIG. 8C). The staining shows cells on both sides of the membrane in both conditions, but mainly in the top channel. In both conditions, there was positive staining for both marker, indicating osteogenic differentiation, however the staining is more prominent in the Bone-Chips that were cultured under flow. After staining against Collagen-1 in the whole chip, confocal microscopy revealed prominent expression in the flow group, while only mild expression was detected in the static cultured chip, comparing to null expression in the control group (FIG. 8D).

The invention claimed is:
1. A non-destructive, live cell molecular labeling and imaging method, comprising:
seeding mesenchymal stem cells (MSCs) that are capable of controllably expressing Bone Morphogenetic Protein-2 (BMP-2) under Tet-Off system and continuously express Luciferase reporter genes under constitutive promoter on a microfluidic device;
culturing the MSCs in culture medium supplemented with doxycycline, tetracycline, or an analogue of tetracycline to prevent BMP-2 expression in the absence of BMP-2 and the absence of flow of the culture medium;
subsequently flowing the culture medium in the absence of BMP-2 such that the MSCs proliferate to produce confluent MSCs;
subsequently culturing the MSCs under constant flow of osteogenic media deficient in doxycycline, tetracycline, and an analogue of tetracycline and containing BMP-2, β-glycerophosphate, and L-Ascorbic acid, the culture medium replaced by the osteogenic media, to promote BMP-2 expression and differentiate the MSCs overexpressing BMP-2 into osteoblasts and/or osteocytes;

adding one or more labeling agents to the microfluidic device such that the one or more labeling agents bind to a marker of cellular differentiation in the microfluidic device; and detecting, over a period of time, the labeling agent in the MSCs, osteoblasts, and/or osteocytes without fixation to measure cellular differentiation, wherein the detecting comprises live cell imaging of the entire microfluidic device including the MSCs, osteoblasts, and/or osteocytes, and wherein survival and proliferation of the MSCs, osteoblasts, and/or osteocytes are non-invasively monitored in real time by quantifying expression of the Luciferase reporter gene using bioluminescence imaging.

2. The method of claim 1, wherein the microfluidic device further comprises one or more channels for loading of a control sample.

3. The method of claim 1, wherein the one or more labeling agents comprise bisphosphonate imaging agents.

4. The method of claim 3, wherein the bisphosphonate imaging agent comprises a pamidronate backbone with a fluorescent label.

5. The method of claim 1, wherein the one or more labeling agents comprise a NHS ester.

6. The method of claim 5, wherein the one or more labeling agents comprise a iminodiacetic acid group.

7. The method of claim 1, wherein detecting the labeling agent comprises fluorescent imaging.

8. The method of claim 1, wherein detecting the labeling agent comprises near infrared imaging.

9. The method of claim 1, further comprising loading one or more control samples, detecting the labeling agent in the one or more control samples, and comparing a quantity of the detected labeling agent in the MSCs, osteoblasts, and/or osteocytes with a quantity of the detected labeling agent in the one or more control samples.

10. The method of claim 1, wherein detecting the labeling agent measures cellular mineralization, wherein the labeling agent detects cellular mineralization.

11. The method of claim 1, wherein detecting the labeling agent measures metabolic function.

12. The method of claim 1, wherein detecting the labeling agent measures inflammation.

13. The method of claim 1, further comprising addition of an exogenous factor to the microfluidic device, the exogenous factor including cytokines including tumor necrosis factor-alpha (TNF-alpha) and interleukin-17 (IL-17) and/or a therapeutic agent including parathyroid hormone.

14. The method of claim 1, subsequent to detecting the labeling agent, further comprising:
continuing to culture the MSCs, osteoblasts, and/or osteocytes in the microfluidic device; and
then detecting the labeling agent again in the MSCs, osteoblasts, and/or osteocytes without fixation.

15. The method of claim 1, wherein the MSCs are derived from induced pluripotent stem cells (iPSCs).

16. The method of claim 15, wherein the iPSCs are derived from a subject afflicted with a disease or condition.

17. The method of claim 16, wherein the disease is a skeletal disease or condition.

18. The method of claim 1, wherein the constant flow is set to 30 μl/hour.

19. The method of claim 1, wherein the marker of cellular differentiation includes one or more osteogenic markers including osteocalcin, bone sialoprotein (bsp), osteopontin (opn), and collagen type 1.

20. The method of claim 19, wherein the osteoblasts and/or osteocytes differentiated from the MSCs express the one or more osteogenic markers.

21. The method of claim 20, wherein the osteoblasts and/or osteocytes differentiated from the MSCs express a higher level of the one or more osteogenic markers compared to the MSCs.

* * * * *